(12) United States Patent
Sakamoto

(10) Patent No.: US 10,273,322 B2
(45) Date of Patent: Apr. 30, 2019

(54) POLYMERIZABLE COMPOUND, POLYMERIZABLE COMPOSITION, POLYMER, AND OPTICAL ANISOTROPIC BODY

(71) Applicant: ZEON CORPORATION, Tokyo (JP)

(72) Inventor: Kei Sakamoto, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 530 days.

(21) Appl. No.: 14/913,233

(22) PCT Filed: Aug. 14, 2014

(86) PCT No.: PCT/JP2014/071428
§ 371 (c)(1),
(2) Date: Feb. 19, 2016

(87) PCT Pub. No.: WO2015/025793
PCT Pub. Date: Feb. 26, 2015

(65) Prior Publication Data
US 2016/0200841 A1 Jul. 14, 2016

(30) Foreign Application Priority Data

Aug. 22, 2013 (JP) .................................. 2013-172739

(51) Int. Cl.
| | | |
|---|---|---|
| *G02F 1/1333* | (2006.01) | |
| *C08F 122/24* | (2006.01) | |
| *C07D 277/82* | (2006.01) | |
| *C08F 222/10* | (2006.01) | |
| *C08F 122/12* | (2006.01) | |
| *C08F 220/30* | (2006.01) | |

(52) U.S. Cl.
CPC .......... *C08F 122/24* (2013.01); *C07D 277/82* (2013.01); *C08F 122/12* (2013.01); *C08F 222/10* (2013.01); *C08F 220/30* (2013.01); *C08F 222/1006* (2013.01)

(58) Field of Classification Search
CPC .... C08F 122/24; C08F 122/12; C08F 222/10; C08F 222/1006; C08F 220/30; C08F 2222/102; C08F 2222/103; C07D 277/82; G02F 1/1333
USPC .......................................................... 526/77
See application file for complete search history.

(56) References Cited

U.S. PATENT DOCUMENTS

| | | | |
|---|---|---|---|
| 5,567,349 A | 10/1996 | Kelly et al. | |
| 6,139,771 A | 10/2000 | Walba et al. | |
| 6,203,724 B1 | 3/2001 | Reiffenrath et al. | |
| 6,565,974 B1 | 5/2003 | Uchiyama et al. | |
| 9,029,490 B2 | 5/2015 | Sakamoto et al. | |
| 9,150,677 B2 | 10/2015 | Sakamoto et al. | |

(Continued)

FOREIGN PATENT DOCUMENTS

| | | |
|---|---|---|
| JP | 10-68816 A | 3/1998 |
| JP | 10-90521 A | 4/1998 |

(Continued)

OTHER PUBLICATIONS

Extended European Search Report dated Apr. 24, 2017 issued in European Patent Application 14838141.1.
International Search Report, issued in PCT/JP2014/071428, dated Oct. 28, 2014.
Written Opinion of the International Searching Authority, issued in PCT/JP2014/071428 (PCT/ISA/237), dated Oct. 28, 2014.

*Primary Examiner* — Geraldina Visconti
(74) *Attorney, Agent, or Firm* — Birch, Stewart, Kolasch & Birch, LLP

(57) ABSTRACT

The present invention relates to: a polymerizable compound represented by a formula (I), wherein each of $Y^1$ to $Y^8$ independently represents —O—, —O—C(=O)—, —C(=O)—O— or the like; each of $A^2$, $A^3$, $G^1$, and $G^2$ independently represents a divalent linear aliphatic group having 1 to 20 carbon atoms or the like; each of $Z^1$ and $Z^2$ independently represents an alkenyl group having 2 to 10 carbon atoms or the like; $A^x$ represents an organic group having 2 to 30 carbon atoms that includes at least one aromatic ring; $A^y$ represents a hydrogen atom, an alkyl group having 1 to 20 carbon atoms or the like; $A^1$ represents a trivalent aromatic group or the like; each of $A^4$ and $A^5$ independently represents a divalent aromatic group having 6 to 30 carbon atoms or the like; and $Q^1$ represents a hydrogen atom, an alkyl group having 1 to 6 carbon atoms or the like; and others. According to the present invention, it becomes possible to provide: a polymerizable compound that have a practical low melting point, exhibit excellent solubility in a general-purpose solvent, can be produced inexpensively, can be dried at a lower temperature, has excellent energy efficiency, and can produce an optical film that achieves uniform conversion of polarized light over a wide wavelength band; and others.

(I)

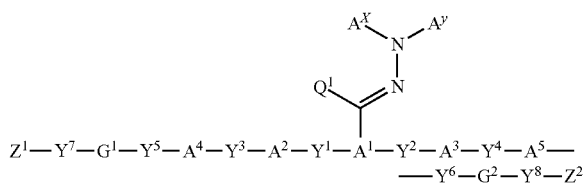

13 Claims, No Drawings

(56) References Cited

U.S. PATENT DOCUMENTS

| | | | |
|---|---|---|---|
| 9,207,360 B2* | 12/2015 | Sakamoto | C07D 215/38 |
| 2002/0159005 A1 | 10/2002 | Arakawa et al. | |
| 2003/0102458 A1 | 6/2003 | Nishikawa et al. | |
| 2007/0176145 A1 | 8/2007 | Nishikawa et al. | |
| 2007/0298191 A1 | 12/2007 | Yamahara et al. | |
| 2009/0072194 A1 | 3/2009 | Yamahara et al. | |
| 2009/0189120 A1 | 7/2009 | Takeuchi | |
| 2010/0201920 A1 | 8/2010 | Adlem et al. | |
| 2010/0301271 A1 | 12/2010 | Adlem et al. | |
| 2014/0107247 A1 | 4/2014 | Sakamoto et al. | |
| 2015/0277010 A1 | 10/2015 | Aimatsu et al. | |
| 2016/0280672 A1* | 9/2016 | Sakamoto | C07D 417/12 |
| 2018/0072952 A1* | 3/2018 | Ikeda | C09K 19/38 |

FOREIGN PATENT DOCUMENTS

| | | |
|---|---|---|
| JP | 11-52131 A | 2/1999 |
| JP | 2000-284126 A | 10/2000 |
| JP | 2001-4837 A | 1/2001 |
| JP | 2002-267838 A | 9/2002 |
| JP | 2003-160540 A | 6/2003 |
| JP | 2005-208414 A | 8/2005 |
| JP | 2005-208415 A | 8/2005 |
| JP | 2005-208416 A | 8/2005 |
| JP | 2005-289980 A | 10/2005 |
| JP | 2005-336103 A | 12/2005 |
| JP | 2006-330710 A | 12/2006 |
| JP | 2007-2208 A | 1/2007 |
| JP | 2009-173893 A | 8/2009 |
| JP | 2009-179563 A | 8/2009 |
| JP | 2009-274984 A | 11/2009 |
| JP | 2010-30979 A | 2/2010 |
| JP | 2010-31223 A | 2/2010 |
| JP | 2010-537954 A | 12/2010 |
| JP | 2010-537955 A | 12/2010 |
| JP | 2011-6360 A | 1/2011 |
| JP | 2011-6361 A | 1/2011 |
| JP | 2011-42606 A | 3/2011 |
| WO | WO 00/26705 A1 | 5/2000 |
| WO | WO 2006/052001 A1 | 5/2006 |
| WO | WO 2012/141245 A1 | 10/2012 |
| WO | WO 2012/147904 A1 | 11/2012 |
| WO | WO 2012/169424 A1 | 12/2012 |
| WO | WO 2012/176679 A1 | 12/2012 |
| WO | WO 2013/018526 A1 | 2/2013 |
| WO | WO 2014/065243 A1 | 5/2014 |

* cited by examiner

POLYMERIZABLE COMPOUND, POLYMERIZABLE COMPOSITION, POLYMER, AND OPTICAL ANISOTROPIC BODY

TECHNICAL FIELD

The present invention relates to a polymerizable compound, a polymerizable composition, and a polymer that can produce an optical film that achieves uniform conversion of polarized light over a wide wavelength band, and also relates to an optically anisotropic article.

BACKGROUND ART

A flat panel display (FPD) that utilizes an optical film (e.g., polarizer and retardation film) can achieve high-resolution display, and has been widely used as a display device that exhibits excellent performance.

A quarter-wave plate that converts linearly polarized light into circularly polarized light, a half-wave plate that changes the plane of vibration of linearly polarized light by 90°, and the like are known as the retardation film. Such a retardation film can achieve accurate conversion of specific monochromatic light so that ¼λ or ½λ retardation occurs.

However, a known retardation film has a problem in that polarized light that passes through is converted into colored polarized light. Specifically, since a material that forms the retardation film has wavelength dispersion with respect to retardation, and a polarization state distribution corresponding to each wavelength occurs with respect to white light that includes different light rays in the visible region, it is impossible to achieve accurate ¼λ, or ½λ retardation over the entire wavelength band.

In order to solve the above problem, various types of wideband retardation films that can achieve uniform retardation with respect to light over a wide wavelength band (i.e., retardation films having reverse wavelength dispersion) have been studied (see Patent Literature 1 to 6, for example).

It has been desired to reduce the thickness of the flat panel display as much as possible along with an improvement in performance and a reduction in weight of mobile information terminals (e.g., mobile personal computer and mobile phone). Therefore, a reduction in thickness of the retardation film has also been desired.

It has been considered that it is most effective to produce a retardation film by applying a polymerizable composition that includes a low-molecular-weight polymerizable compound to a film substrate in order to reduce the thickness of the retardation film. Various types of low-molecular-weight polymerizable compounds having excellent wavelength dispersion, and polymerizable compositions using such polymerizable compounds have been developed (see Patent Literature 7 to 24, for example).

However, the low-molecular-weight polymerizable compounds or the polymerizable compositions disclosed in Patent Literature 7 to 24 have a number of problems in that reverse wavelength dispersion may be insufficient, or it may be difficult to apply the low-molecular-weight polymerizable compounds or the polymerizable compositions to a film due to a high melting point that is not suitable for an industrial process, or the temperature range in which liquid crystallinity is obtained may be very narrow, or solubility in a solvent generally used for an industrial process may be low. Moreover, since these low-molecular-weight polymerizable compounds and the like are synthesized by performing a plurality of steps using a synthesis method that utilizes an expensive reagent, the production cost increases.

CITATION LIST

Patent Literature

Patent Literature 1: JP-A-10-68816
Patent Literature 2: JP-A-10-90521
Patent Literature 3: JP-A-11-52131
Patent Literature 4: JP-A-2000-284126 (US20020159005A1)
Patent Literature 5: JP-A-2001-4837
Patent Literature 6: WO2000/026705
Patent Literature 7: JP-A-2002-267838
Patent Literature 8: JP-A-2003-160540 (US20030102458A1)
Patent Literature 9: JP-A-2005-208414
Patent Literature 10: JP-A-2005-208415
Patent Literature 11: JP-A-2005-208416
Patent Literature 12: JP-A-2005-289980 (US20070176145A1)
Patent Literature 13: JP-A-2006-330710 (US20090072194A1)
Patent Literature 14: JP-A-2009-179563 (US20090189120A1)
Patent Literature 15: JP-A-2010-31223
Patent Literature 16: JP-A-2011-6360
Patent Literature 17: JP-A-2011-6361
Patent Literature 18: JP-A-2011-42606
Patent Literature 19: JP-T-2010-537954 (US20100201920A1)
Patent Literature 20: JP-T-2010-537955 (US20100301271A1)
Patent Literature 21: WO2006/052001 (US20070298191A1)
Patent Literature 22: U.S. Pat. No. 6,139,771
Patent Literature 23: U.S. Pat. No. 6,203,724
Patent Literature 24: U.S. Pat. No. 5,567,349

SUMMARY OF INVENTION

Technical Problem

The invention was conceived in view of the above situation. An object of the invention is to provide a polymerizable compound, a polymerizable composition, and a polymer that have a practical low melting point, exhibit excellent solubility in a general-purpose solvent, can be produced inexpensively, and can produce an optical film that achieves uniform conversion of polarized light over a wide wavelength band, and an optically anisotropic article.

Solution to Problem

The inventors of the invention conducted extensive studies in order to solve the above problem. As a result, the inventors found that an optical film that achieves uniform conversion of polarized light over a wide wavelength band, and exhibits satisfactory performance can be produced inexpensively by utilizing an optically anisotropic article that is produced using a polymer that is obtained by polymerizing a polymerizable compound represented by the following formula (I), or polymerizing a polymerizable composition that includes the polymerizable compound and an initiator. This finding has led to the completion of the invention.

Several aspects of the invention provide the following polymerizable compound (see (1) to (7)), polymerizable composition (see (8) and (9)), polymer (see (10) and (11)), and optically anisotropic article (see (12)).

(1) A polymerizable compound represented by the following formula (I),

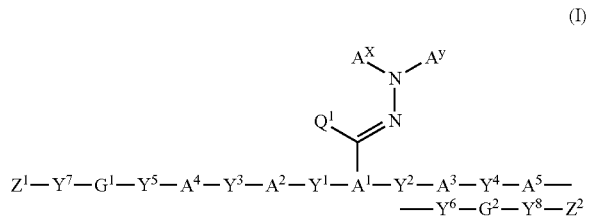

$Z^1-Y^7-G^1-Y^5-A^4-Y^3-A^2-Y^1-A^1-Y^2-A^3-Y^4-A^5--$
$\quad\quad\quad\quad\quad\quad\quad\quad\quad\quad\quad\quad\quad--Y^6-G^2-Y^8-Z^2$ wherein each of $Y^1$ to $Y^8$ independently represents a chemical single bond, —O—, —S—, —O—C(=O)—, —C(=O)—O—, —O—C(=O)—O—, —NR$^1$—C(=O)—, —C(=O)—NR$^1$—, —O—C(=O)—NR$^1$—, —NR$^1$—C(=O)—O—, —NR$^1$—C(=O)—NR$^1$, —O—NR$^1$—, or —NR$^1$—O—, R$^1$ is a hydrogen atom or an alkyl group having 1 to 6 carbon atoms, each of A$^2$, A$^3$, G$^1$, and G$^2$ independently represents a substituted or unsubstituted divalent linear aliphatic group having 1 to 20 carbon atoms that optionally includes —O—, —S—, —O—C(=O)—, —C(=O)—O—, —O—C(=O)—O—, —NR$^2$—C(=O)—, —C(=O)—NR$^2$—, —NR$^2$—, or —C(=O)—, provided that a case where the linear aliphatic group includes two or more contiguous —O— or —S— is excluded, R$^2$ is a hydrogen atom or an alkyl group having 1 to 6 carbon atoms, each of $Z^1$ and $Z^2$ independently represents an alkenyl group having 2 to 10 carbon atoms that is substituted with a halogen atom, or unsubstituted, A$^x$ is an organic group having 2 to 30 carbon atoms that includes at least one aromatic ring selected from the group consisting of an aromatic hydrocarbon ring and an aromatic heterocyclic ring, A$^Y$ is a hydrogen atom, a substituted or unsubstituted alkyl group having 1 to 20 carbon atoms, a substituted or unsubstituted alkenyl group having 2 to 20 carbon atoms, a substituted or unsubstituted cycloalkyl group having 3 to 12 carbon atoms, a substituted or unsubstituted alkynyl group having 2 to 20 carbon atoms, —C(=O)—R$^3$; —SO$_2$—R$^4$, —C(=S)NH—R$^5$, or an organic group having 2 to 30 carbon atoms that includes at least one aromatic ring selected from the group consisting of an aromatic hydrocarbon ring and an aromatic heterocyclic ring, R$^3$ is a substituted or unsubstituted alkyl group having 1 to 20 carbon atoms, a substituted or unsubstituted alkenyl group having 2 to 20 carbon atoms, or a substituted or unsubstituted cycloalkyl group having 3 to 12 carbon atoms, R$^4$ is an alkyl group having 5 to 20 carbon atoms, an alkenyl group having 2 to 20 carbon atoms, a phenyl group, or a 4-methylphenyl group, R$^5$ is a substituted or unsubstituted alkyl group having 1 to 20 carbon atoms, a substituted or unsubstituted alkenyl group having 2 to 20 carbon atoms, a substituted or unsubstituted cycloalkyl group having 3 to 12 carbon atoms, or a substituted or unsubstituted aromatic group having 5 to 20 carbon atoms, provided that the aromatic ring included in A$^x$ and the aromatic ring optionally included in A$^Y$ are either substituted or unsubstituted, and A$^x$ and A$^y$ are optionally bonded to each other to form a ring, A$^1$ is a substituted or unsubstituted trivalent aromatic group, each of A$^4$ and A$^5$ independently represents a substituted or unsubstituted divalent aromatic group having 6 to 30 carbon atoms, and Q$^1$ is a hydrogen atom, or a substituted or unsubstituted alkyl group having 1 to 6 carbon atoms.

(2) The polymerizable compound according to (1), wherein the total number of π electrons included in A$^x$ and A$^y$ is 4 to 24.

(3) The polymerizable compound according to (1) or (2), wherein A$^1$ is a substituted or unsubstituted trivalent benzene ring group, or a substituted or unsubstituted trivalent naphthalene ring group.

(4) The polymerizable compound according to any one of (1) to (3), wherein each of $Y^1$ to $Y^8$ independently represents a chemical single bond, —O—, —O—C(=O)—, —C(=O)—O—, or —O—C(=O)—O—.

(5) The polymerizable compound according to any one of (1) to (4), wherein each of $Z^1$ and $Z^2$ independently represents CH$_2$=CH—, CH$_2$=C(CH$_3$)—, or CH$_2$=C(Cl)—.

(6) The polymerizable compound according to any one of (1) to (5), wherein each of A$^2$, A$^3$, G$^1$, and G$^2$ independently represents a substituted or unsubstituted divalent linear aliphatic group having 1 to 20 carbon atoms that optionally includes —O—, —O—C(=O)—, —C(=O)—O—, or —C(=O)—, provided that a case where the linear aliphatic group includes two or more contiguous —O— is excluded.

(7) The polymerizable compound according to any one of (1) to (6), wherein each of G$^1$ and G$^2$ independently represents an alkylene group having 1 to 12 carbon atoms.

(8) A polymerizable composition including at least one type of the polymerizable compound according to any one of (1) to (7).

(9) A polymerizable composition including at least one type of the polymerizable compound according to any one of (1) to (7), and an initiator.

(10) A polymer obtained by polymerizing the polymerizable compound according to any one of (1) to (7), or polymerizing the polymerizable composition according to (8) or (9).

(11) The polymer according to (10), the polymer being a liquid crystalline polymer.

(12) An optically anisotropic article including the polymer according to (11).

ADVANTAGEOUS EFFECTS OF INVENTION

The polymerizable compound, the polymerizable composition, and the polymer according to the aspects of the invention make it possible to inexpensively produce an optically anisotropic article that achieves uniform conversion of polarized light over a wide wavelength band, and exhibits satisfactory performance. Since the drying temperature employed when forming a liquid crystal layer can be reduced by utilizing the polymerizable composition that includes the polymerizable compound, it is possible to improve the energy efficiency, and reduce the cost required to produce a liquid crystal polymer film.

Since the optically anisotropic article according to one aspect of the invention is produced using the polymer according to one aspect of the invention, the optically anisotropic article can be produced inexpensively, can achieve uniform conversion of polarized light over a wide wavelength band, and exhibits satisfactory performance.

An antireflective film can be produced by combining the optically anisotropic article according to one aspect of the invention (that is formed in the shape of a film) with a polarizer. The antireflective film may suitably be used to prevent reflection from a touch panel, an organic electroluminescence device, and the like.

DESCRIPTION OF EMBODIMENTS

A polymerizable compound, a polymerizable composition, a polymer, and an optically anisotropic article according to the exemplary embodiments of the invention are described in detail below.

1) Polymerizable Compound

A polymerizable compound according to one embodiment of the invention is a compound represented by the formula (I).

each of $Y^1$ to $Y^8$ in the formula (I) independently represents a chemical single bond, —O—, —S—, —O—C(=O)—, —C(=O)—O—, —O—C(=O)—O—, —$NR^1$—C(=O)—, —C(=O)—$NR^1$—, —O—C(=O)—$NR^1$—, —$NR^1$—C(=O)—O—, —$NR^1$—C(=O)—$NR^1$—, —O—$NR^1$—, or —$NR^1$—O—.

$R^1$ is a hydrogen atom or an alkyl group having 1 to 6 carbon atoms.

Examples of the alkyl group having 1 to 6 carbon atoms represented by $R^1$ include a methyl group, an ethyl group, an n-propyl group, an isopropyl group, an n-butyl group, a sec-butyl group, a t-butyl group, an n-pentyl group, an n-hexyl group, and the like.

$R^1$ is preferably a hydrogen atom or an alkyl group having 1 to 4 carbon atoms.

It is preferable that $Y^1$ to $Y^8$ included in the polymerizable compound according to one embodiment of the invention be each independently a chemical single bond, —O—, —O—C(=O)—, —C(=O)—O—, or —O—C(=O)—O—.

Each of $A^2$, $A^3$, $G^1$, and $G^2$ independently represents a substituted or unsubstituted divalent linear aliphatic group having 1 to 20 carbon atoms. Note that the expression "substituted or unsubstituted" used herein in connection with a group or the like means that the group or the like is unsubstituted, or substituted with a substituent (hereinafter the same).

Examples of the divalent linear aliphatic group having 1 to 20 carbon atoms include an alkylene group having 1 to 20 carbon atoms, such as a methylene group, an ethylene group, a trimethylene group, a propylene group, a tetramethylene group, a pentamethylene group, a hexamethylene group, an octamethylene group, and a decamethylene group-(—$(CH_2)_{10}$—); an alkenylene group having 2 to 20 carbon atoms, such as a vinylene group, a 1-methylvinylene group, a propenylene group, a 1-butenylene group, a 2-butenylene group, a 1-pentenylene group, and a 2-pentenylene group; and the like.

Examples of a substituent that may substitute the divalent linear aliphatic group represented by $A^2$, $A^3$, $G^1$, and $G^2$ include a halogen atom such as a fluorine atom, a chlorine atom, a bromine atom, and an iodine atom; an alkoxy group having 1 to 6 carbon atoms, such as a methoxy group, an ethoxy group, an n-propoxy group, an isopropoxy group, an n-butoxy group, a sec-butoxy group, a t-butoxy group, an n-pentyloxy group, and an n-hexyloxy group; and the like. Among these, a fluorine atom, a methoxy group, and an ethoxy group are preferable.

The linear aliphatic group optionally includes —O—, —S—, —O—C(=O)—, —C(=O)—O—, —O—C(=O)—O—, —$NR^2$—C(=O)—, —C(=O)—$NR^2$—, —$NR^2$—, or —C(=O)— (provided that a case where the linear aliphatic group includes two or more contiguous —O— or —S— is excluded). $R^2$ is a hydrogen atom or an alkyl group having 1 to 6 carbon atoms similar to that represented by $R^1$, and is preferably a hydrogen atom or a methyl group.

—O—, —O—C(=O)—, —C(=O)—O—, and —C(=O)— are preferable as the group that is optionally included in the linear aliphatic group.

Specific examples of the linear aliphatic group that includes the above group include —$CH_2$—$CH_2$—O—$CH_2$—$CH_2$—, —$CH_2$—$CH_2$—S—$CH_2$—$CH_2$—, —$CH_2$—$CH_2$—O—C(=O)—$CH_2$—$CH_2$—, —$CH_2$—$CH_2$—C(=O)—O—$CH_2$—$CH_2$—, —$CH_2$—$CH_2$—C(=O)—O—$CH_2$—, —$CH_2$—O—C(=O)—O—$CH_2$—$CH_2$—, —$CH_2$—$CH_2$—$NR^2$—C(=O)—$CH_2$—$CH_2$—, —$CH_2$—$CH_2$—C(=O)—$NR^2$—$CH_2$—, —$CH_2$—$NR^2$—$CH_2$—$CH_2$—, —$CH_2$—C(=O)—$CH_2$—, and the like.

It is preferable that each of $A^2$ and $A^3$ independently represent a divalent linear aliphatic group such as an alkylene group having 1 to 20 carbon atoms or an alkenylene group having 2 to 20 carbon atoms, more preferably an alkylene group having 1 to 12 carbon atoms, and particularly preferably a tetramethylene group (—$(CH_2)_4$—), a hexamethylene group (—$(CH_2)_6$—), an octamethylene group (—$(CH_2)_8$—), or a decamethylene group (—$(CH_2)_{10}$—), in order to more advantageously achieve the intended effects of the invention.

It is preferable that each of $G^1$ and $G^2$ independently represent a substituted or unsubstituted divalent linear aliphatic group having 1 to 12 carbon atoms (that optionally includes —O—, —O—C(=O)—, —C(=O)—O—, or —C(=O)—, provided that a case where the aliphatic group includes two or more contiguous —O— is excluded), more preferably a divalent linear aliphatic group such as an alkylene group having 1 to 12 carbon atoms or an alkenylene group having 2 to 20 carbon atoms, still more preferably an alkylene group having 1 to 12 carbon atoms, and particularly preferably a tetramethylene group (—$(CH_2)_4$—),
a hexamethylene group (—$(CH_2)_6$—), an octamethylene group (—$(CH_2)_8$—), or
a decamethylene group (—$(CH_2)_{10}$—).

Each of $Z^1$ and $Z^2$ independently represents an alkenyl group having 2 to 10 carbon atoms that is substituted with a halogen atom, or unsubstituted.

The number of carbon atoms of the alkenyl group is preferably 2 to 6.

Examples of the halogen atom that may substitute the alkenyl group represented by $Z^1$ and $Z^2$ include a fluorine atom, a chlorine atom, a bromine atom, and the like. Among these, a chlorine atom is preferable.

Specific examples of the alkenyl group having 2 to 10 carbon atoms represented by $Z^1$ and $Z^2$ include $CH_2$=CH—, $CH_2$=C($CH_3$)—, $CH_2$=CH—$CH_2$—, $CH_3$—CH=CH—, $CH_2$=CH—$CH_2$—$CH_2$—, $CH_2$=C($CH_3$)—$CH_2$—$CH_2$—, $(CH_3)_2$C=CH—$CH_2$—, $(CH_3)_2$C=CH—$CH_2$—$CH_2$—, $CH_2$=C(Cl)—, $CH_2$=C($CH_3$)—$CH_2$—, $CH_3$—CH=CH—$CH_2$—, and the like.

It is preferable that each of $Z^1$ and $Z^2$ independently represent $CH_2$=CH—, $CH_2$=C($CH_3$)—, $CH_2$=C(Cl)—, $CH_2$=CH—$CH_2$—, $CH_2$=C($CH_3$)—$CH_2$—, or $CH_2$=C($CH_3$)—$CH_2$—$CH_2$—, more preferably $CH_2$=CH—, $CH_2$=C($CH_3$)—, or $CH_2$=C(Cl)—, and still more preferably $CH_2$=CH—, in order to more advantageously achieve the intended effects of the invention.

$A^x$ is an organic group having 2 to 30 carbon atoms that includes at least one aromatic ring selected from the group consisting of an aromatic hydrocarbon ring and an aromatic heterocyclic ring.

The term "aromatic ring" used herein refers to a cyclic structure that exhibits aromaticity in a broad sense according to Huckel's rule (i.e., a cyclic conjugated structure that includes (4n+2) π electrons, and a structure that exhibits aromaticity in which a lone electron pair of a hetero atom (e.g., sulfur, oxygen, or nitrogen) is involved in the π electron system (e.g., thiophene, furan, and benzothiazole)).

The organic group having 2 to 30 carbon atoms represented by $A^x$ that includes at least one aromatic ring selected from the group consisting of an aromatic hydrocarbon ring and an aromatic heterocyclic ring, may include a plurality of aromatic rings, and may include an aromatic hydrocarbon ring and an aromatic heterocyclic ring.

Examples of the aromatic hydrocarbon ring include a benzene ring, a naphthalene ring, an anthracene ring, and the like. Examples of the aromatic heterocyclic ring include a monocyclic aromatic heterocyclic ring such as a pyrrole ring,
a furan ring,
a thiophene ring, a pyridine ring, a pyridazine ring, a pyrimidine ring, a pyrazine ring,
a pyrazole ring, an imidazole ring, an oxazole ring, and a thiazole ring; a fused aromatic
heterocyclic ring such as a benzothiazole ring, a benzoxazole ring, a quinoline ring,
a phthalazine ring, a benzimidazole ring, a benzopyrazole ring, a benzofuran ring,
a benzothiophene ring, a thiazolopyridine ring, an oxazolopyridine ring,
a thiazolopyrazine ring, an oxazolopyrazine ring, a thiazolopyridazine ring,
an oxazolopyridazine ring, a thiazolopyrimidine ring, and an oxazolopyrimidine ring; and the like.

The aromatic ring included in $A^x$ may be substituted with a substituent. Examples of the substituent include a halogen atom such as a fluorine atom and a chlorine atom; a cyano group; an alkyl group having 1 to 6 carbon atoms, such as a methyl group, an ethyl group, and a propyl group; an alkenyl group having 2 to 6 carbon atoms, such as a vinyl group and an allyl group; an alkyl halide group having 1 to 6 carbon atoms, such as a trifluoromethyl group; a substituted amino group such as a dimethylamino group; an alkoxy group having 1 to 6 carbon atoms, such as a methoxy group, an ethoxy group, and an isopropoxy group; a nitro group; an aryl group such as a phenyl group and a naphthyl group; —C(=O)—$R^6$; —C(=O)—$OR^6$; —$SO_2R^7$; and the like. $R^6$ is an alkyl group having 1 to 20 carbon atoms, an alkenyl group having 2 to 20 carbon atoms, or a cycloalkyl group having 3 to 12 carbon atoms, and $R^7$ is an alkyl group having 1 to 20 carbon atoms, an alkenyl group having 2 to 20 carbon atoms, a phenyl group, or a 4-methylphenyl group similar to that represented by $R^4$.

The aromatic ring included in $A^x$ may be substituted with a plurality of identical or different substituents, and two adjacent substituents may be bonded to each other to form a ring. A ring formed by two adjacent substituents may be either a monocyclic ring or a fused polycyclic ring, and may be either an unsaturated ring or a saturated ring.

Note that the number of carbon atoms (i.e., 2 to 30) of the organic group represented by $A^x$ refers to the total number of carbon atoms of the organic group excluding the number of carbon atoms of a substituent. This also applies to the number of carbon atoms of the organic group that may be represented by $A^y$.

Examples of the organic group having 2 to 30 carbon atoms represented by $A^x$ (that includes at least one aromatic ring selected from the group consisting of an aromatic hydrocarbon ring and an aromatic heterocyclic ring) include an aromatic hydrocarbon ring group; an aromatic heterocyclic group; an alkyl group having 3 to 30 carbon atoms that includes at least one aromatic ring selected from the group consisting of an aromatic hydrocarbon ring and an aromatic heterocyclic ring; an alkenyl group having 4 to 30 carbon atoms that includes at least one aromatic ring selected from the group consisting of an aromatic hydrocarbon ring and an aromatic heterocyclic ring; an alkynyl group having 4 to 30 carbon atoms that includes at least one aromatic ring selected from the group consisting of an aromatic hydrocarbon ring and an aromatic heterocyclic ring; and the like.

Specific examples of the organic group represented by $A^x$ are as follows. Note that the organic group represented by $A^x$ is not limited to the following groups. "—" in the following formulas is a bond from the ring (hereinafter the same).

(1) Aromatic hydrocarbon ring group

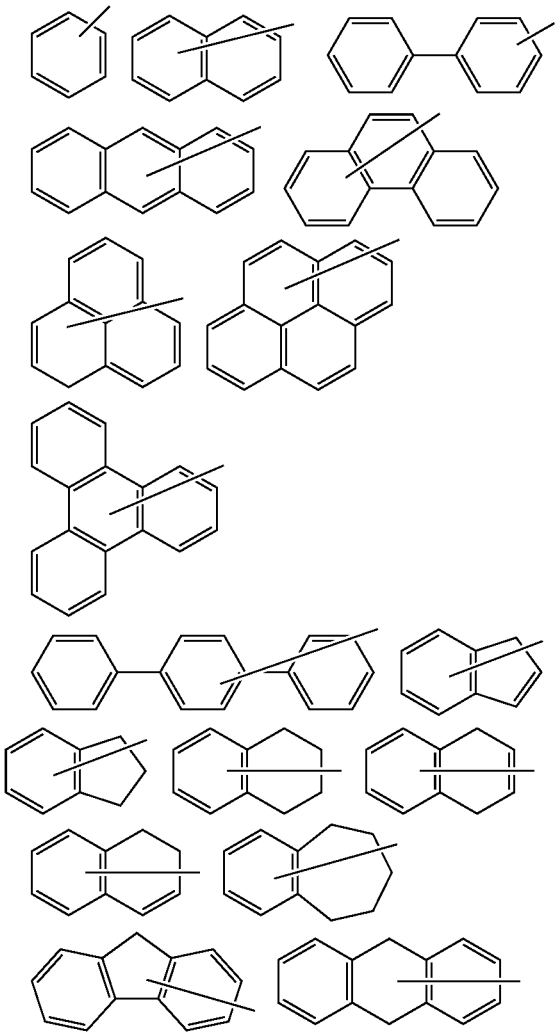

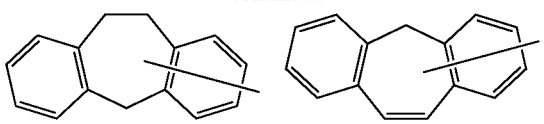

(2) Aromatic heterocyclic ring group

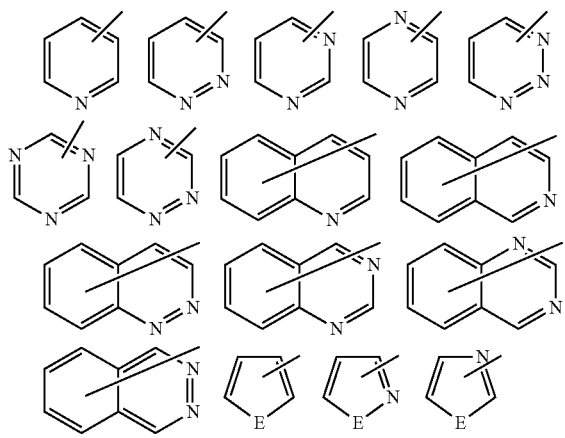

wherein E is NR⁸, an oxygen atom, or a sulfur atom, and R⁸ is a hydrogen atom, or an alkyl group having 1 to 6 carbon atoms (e.g., methyl group, ethyl group, or propyl group).

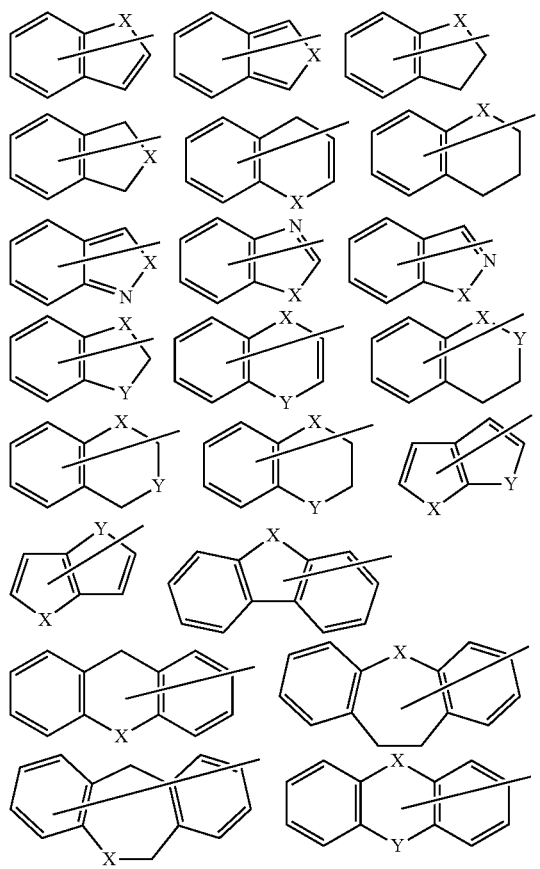

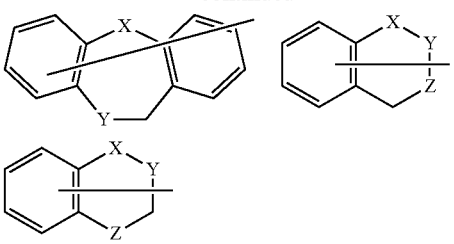

wherein each of X, Y, and Z independently represents $NR^8$, an oxygen atom, a sulfur atom, —SO—, or —SO$_2$— (provided that a case where oxygen atoms, sulfur atoms, —SO—, or —SO$_2$— are situated at adjacent positions is excluded) and R⁸ is the same as defined above.

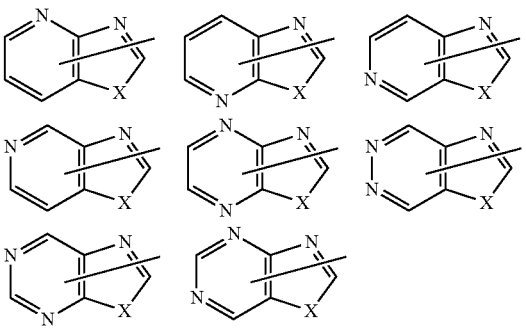

wherein X is the same as defined above.

(3) Alkyl group that includes at least one aromatic ring selected from the group consisting of an aromatic hydrocarbon ring group and an aromatic heterocyclic ring group

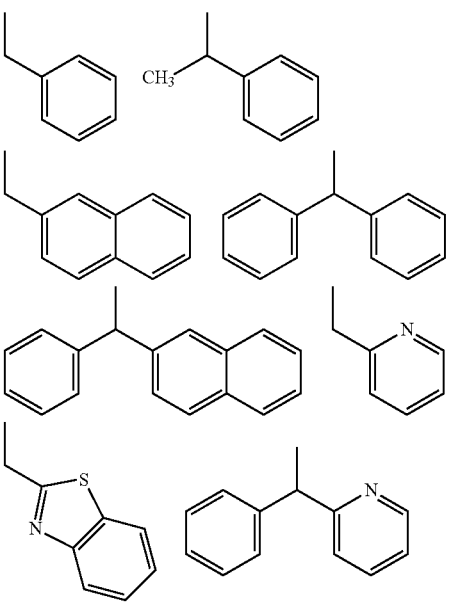

(4) Alkenyl group that includes at least one aromatic ring selected from the group consisting of an aromatic hydrocarbon ring group and an aromatic heterocyclic ring group

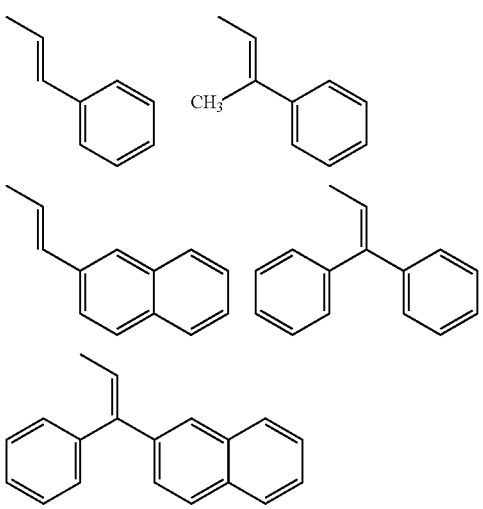

(5) Alkynyl group that includes at least one aromatic ring selected from the group consisting of an aromatic hydrocarbon ring group and an aromatic heterocyclic ring group

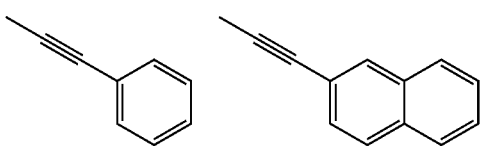

It is preferable that $A^x$ be an aromatic hydrocarbon group having 4 to 30 carbon atoms or an aromatic heterocyclic ring group having 4 to 30 carbon atoms. It is more preferable that $A^x$ be a group among the groups respectively having the following structures.

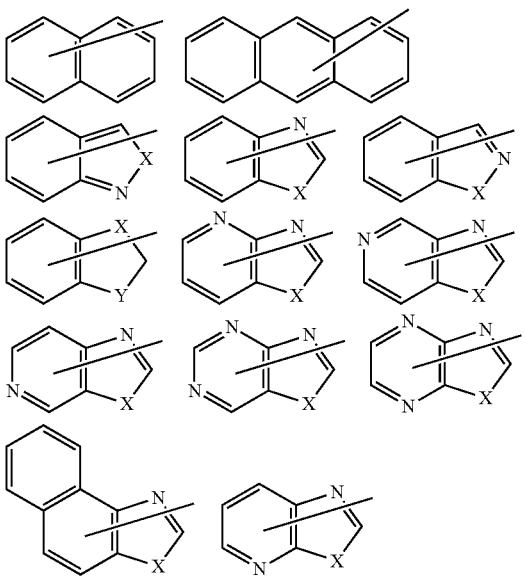

It is still more preferable that $A^x$ be a group among the groups respectively having the following structures.

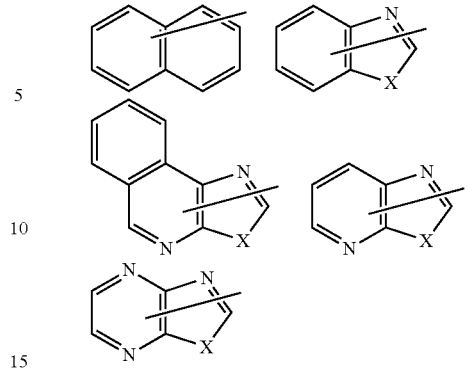

The ring included in $A^x$ may be substituted with a substituent. Examples of the substituent include a halogen atom such as a fluorine atom and a chlorine atom; a cyano group; an alkyl group having 1 to 6 carbon atoms, such as a methyl group, an ethyl group, and a propyl group; an alkenyl group having 2 to 6 carbon atoms, such as a vinyl group and an allyl group; an alkyl halide group having 1 to 6 carbon atoms, such as a trifluoromethyl group; a substituted amino group such as a dimethylamino group; an alkoxy group having 1 to 6 carbon atoms, such as a methoxy group, an ethoxy group, and an isopropoxy group; a nitro group; an aryl group such as a phenyl group and a naphthyl group; —C(=O)—R$^9$; —C(=O)—OR$^9$; —SO$_2$R$^9$; and the like. R$^9$ is an alkyl group having 1 to 6 carbon atoms (e.g., methyl group or ethyl group), or an aryl group having 6 to 14 carbon atoms (e.g., phenyl group). Among these, a halogen atom, a cyano group, an alkyl group having 1 to 6 carbon atoms, and an alkoxy group having 1 to 6 carbon atoms are preferable.

The ring included in $A^x$ may be substituted with a plurality of identical or different substituents, and two adjacent substituents may be bonded to each other to form a ring. The ring formed by two adjacent substituents may be either a monocyclic ring or a fused polycyclic ring.

Note that the number of carbon atoms (i.e., 2 to 30) of the organic group represented by $A^x$ refers to the total number of carbon atoms of the organic group excluding the number of carbon atoms of a substituent. This also applies to the number of carbon atoms of the organic group that may be represented by $A_y$.

$A^y$ is a hydrogen atom, a substituted or unsubstituted alkyl group having 1 to 20 carbon atoms, a substituted or unsubstituted alkenyl group having 2 to 20 carbon atoms, a substituted or unsubstituted cycloalkyl group having 3 to 12 carbon atoms, a substituted or unsubstituted alkynyl group having 2 to 20 carbon atoms, —C(=O)—R$^3$, —SO$_2$—R$^4$, —C(=S)NH—R$^5$, or an organic group having 2 to 30 carbon atoms that includes at least one aromatic ring selected from the group consisting of an aromatic hydrocarbon ring and an aromatic heterocyclic ring. R$^3$ is a substituted or unsubstituted alkyl group having 1 to 20 carbon atoms, a substituted or unsubstituted alkenyl group having 2 to 20 carbon atoms, a substituted or unsubstituted cycloalkyl group having 3 to 12 carbon atoms, or an aromatic hydrocarbon group having 5 to 12 carbon atoms, R$^4$ is an alkyl group having 1 to 20 carbon atoms, an alkenyl group having 2 to 20 carbon atoms, a phenyl group, or a 4-methylphenyl group, and R$^5$ is a substituted or unsubstituted alkyl group having 1 to 20 carbon atoms, a substituted or unsubstituted alkenyl group having 2 to 20 carbon atoms, a substituted or unsubstituted cycloalkyl group having 3 to 12 carbon atoms, or a substituted or unsubstituted aromatic group having 5 to 20 carbon atoms.

Examples of the alkyl group having 1 to 20 carbon atoms (that is substituted or unsubstituted) represented by $A^y$ include a methyl group, an ethyl group, an n-propyl group, an isopropyl group, an n-butyl group, an isobutyl group, a 1-methylpentyl group, a 1-ethylpentyl group, a sec-butyl group, a t-butyl group, an n-pentyl group, an isopentyl group, a neopentyl group, an n-hexyl group, an isohexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, an n-nonadecyl group, an n-icosyl group, and the like. The number of carbon atoms of the substituted or unsubstituted alkyl group having 1 to 20 carbon atoms is preferably 1 to 12, and more preferably 4 to 10.

Examples of the alkenyl group having 2 to 20 carbon atoms (that is substituted or unsubstituted) represented by $A^y$ include a vinyl group, a propenyl group, an isopropenyl group, a butenyl group, an isobutenyl group, a pentenyl group, a hexenyl group, a heptenyl group, an octenyl group, a decenyl group, an undecenyl group, a dodecenyl group, a tridecenyl group, a tetradecenyl group, a pentadecenyl group, a hexadecenyl group, a heptadecenyl group, an octadecenyl group, a nonadecenyl group, an icosenyl group, and the like.

The number of carbon atoms of the substituted or unsubstituted alkenyl group having 2 to 20 carbon atoms is preferably 2 to 12.

Examples of the cycloalkyl group having 3 to 12 carbon atoms (that is substituted or unsubstituted) represented by $A^y$ include a cyclopropyl group, a cyclobutyl group, a cyclopentyl group, a cyclohexyl group, a cyclooctyl group, and the like.

Examples of the alkynyl group having 2 to 20 carbon atoms (that is substituted or unsubstituted) represented by $A^y$ include an ethynyl group, a propynyl group, a 2-propynyl group (propargyl group), a butynyl group, a 2-butynyl group, a 3-butynyl group, a pentynyl group, a 2-pentynyl group, a hexynyl group, a 5-hexynyl group, a 2-heptynyl group, an octan-2-yn-1-yl group, a nonan-2-yn-1-yl group, a decan-2-yn-1-yl group, a decan-7-yn-1-yl group, and the like.

Examples of a substituent that may substitute the substituted or unsubstituted alkyl group having 1 to 20 carbon atoms and the substituted or unsubstituted alkenyl group having 2 to 20 carbon atoms that may be represented by $A^y$ include a halogen atom such as a fluorine atom and a chlorine atom; a cyano group; a substituted amino group such as a dimethylamino group; an alkoxy group having 1 to 20 carbon atoms, such as a methoxy group, an ethoxy group, an isopropoxy group, and a butoxy group; an alkoxy group having 1 to 12 carbon atoms that is substituted with an alkoxy group having 1 to 12 carbon atoms, such as a methoxymethoxy group and a methoxyethoxy group; a nitro group; an aryl group such as a phenyl group and a naphthyl group;

a cycloalkyl group having 3 to 8 carbon atoms, such as a cyclopropyl group, a cyclopentyl group, and a cyclohexyl group; a cycloalkyloxy group having 3 to 8 carbon atoms, such as a cyclopentyloxy group and a cyclohexyloxy group; a cyclic ether group having 2 to 12 carbon atoms, such as a tetrahydrofuranyl group, a tetrahydropyranyl group, a dioxoranyl group, and a dioxanyl group; an aryloxy group having 6 to 14 carbon atoms, such as a phenoxy group and a naphthoxy group;

a fluoroalkyl group having 1 to 12 carbon atoms in which at least one hydrogen atom is substituted with a fluorine atom, such as a trifluoromethyl group, a pentafluoroethyl group, and a 2,2,2-trifluoroethyl group; a benzofuryl group; a benzopyranyl group;

a benzodioxolyl group; a benzodioxanyl group; —C(=O)—$R^{10}$; —C(=O)—$OR^{10}$; —$SO_2R^4$; —$SR^{10}$; an alkoxy group having 1 to 12 carbon atoms that is substituted with —$SR^{10}$;

a hydroxyl group; and the like. $R^{10}$ is an alkyl group having 1 to 20 carbon atoms, an alkenyl group having 2 to 20 carbon atoms, a cycloalkyl group having 3 to 12 carbon atoms, or an aromatic hydrocarbon group having 6 to 12 carbon atoms, and $R^4$ is the same as defined above.

Examples of a substituent that may substitute the substituted or unsubstituted cycloalkyl group having 3 to 12 carbon atoms that may be represented by $A^y$ include a halogen atom such as a fluorine atom and a chlorine atom; a cyano group; a substituted amino group such as a dimethylamino group; an alkyl group having 1 to 6 carbon atoms, such as a methyl group, an ethyl group, and a propyl group; an alkoxy group having 1 to 6 carbon atoms, such as a methoxy group, an ethoxy group, and an isopropoxy group; a nitro group; an aryl group such as a phenyl group and a naphthyl group; a cycloalkyl group having 3 to 8 carbon atoms, such as a cyclopropyl group, a cyclopentyl group, and a cyclohexyl group; —C(=O)—$R^3$; —C(=O)—$OR^3$; —$SO_2R^4$; a hydroxyl group; and the like. Note that $R^3$ and $R^4$ are the same as defined above.

Examples of a substituent that may substitute the substituted or unsubstituted alkynyl group having 2 to 20 carbon atoms that may be represented by $A^y$ include those mentioned above in connection with the substituted or unsubstituted alkyl group having 1 to 20 carbon atoms, and the substituted or unsubstituted alkenyl group having 2 to 20 carbon atoms.

Examples of the organic group having 2 to 30 carbon atoms represented by $A^y$ that includes at least one aromatic ring selected from the group consisting of an aromatic hydrocarbon ring and an aromatic heterocyclic ring, include those mentioned above in connection with $A^x$.

$A^y$ is preferably a hydrogen atom, a substituted or unsubstituted alkyl group having 1 to 20 carbon atoms, a substituted or unsubstituted alkenyl group having 2 to 20 carbon atoms, a substituted or unsubstituted cycloalkyl group having 3 to 12 carbon atoms, a substituted or unsubstituted alkynyl group having 2 to 20 carbon atoms, —C(=O)—$R^3$, —$SO_2$—$R^4$, or an organic group having 2 to 30 carbon atoms that includes at least one aromatic ring selected from the group consisting of an aromatic hydrocarbon ring and an aromatic heterocyclic ring, and more preferably a hydrogen atom, a substituted or unsubstituted alkyl group having 1 to 20 carbon atoms, a substituted or unsubstituted alkenyl group having 2 to 20 carbon atoms, a substituted or unsubstituted cycloalkyl group having 3 to 12 carbon atoms, a substituted or unsubstituted alkynyl group having 2 to 20 carbon atoms, a substituted or unsubstituted aromatic hydrocarbon group having 6 to 12 carbon atoms, a substituted or unsubstituted aromatic heterocyclic ring group having 3 to 9 carbon atoms, —C(=O)—$R^3$, or —$SO_2$—$R^4$. Note that $R^3$ and $R^4$ are the same as defined above.

Examples of a preferable substituent that may substitute the substituted or unsubstituted alkyl group having 1 to 20 carbon atoms, the substituted or unsubstituted alkenyl group having 2 to 20 carbon atoms, and the substituted or unsubstituted alkynyl group having 2 to 20 carbon atoms, include a halogen atom, a cyano group, an alkoxy group having 1 to 20 carbon atoms, an alkoxy group having 1 to 12 carbon atoms that is substituted with an alkoxy group having 1 to 12 carbon atoms, a phenyl group, a cyclohexyl group, a cyclic ether group having 2 to 12 carbon atoms, an aryloxy group having 6 to 14 carbon atoms, a hydroxyl group, a benzodioxanyl group, and —$SR^{10}$. Note that $R^{10}$ is the same as defined above.

Examples of a preferable substituent that may substitute the substituted or unsubstituted cycloalkyl group having 3 to 12 carbon atoms, the substituted or unsubstituted aromatic hydrocarbon group having 6 to 12 carbon atoms, and the substituted or unsubstituted aromatic heterocyclic ring group having 3 to 9 carbon atoms, include a fluorine atom, an alkyl group having 1 to 6 carbon atoms, an alkoxy group having 1 to 6 carbon atoms, and a cyano group.

$A^x$ and $A^y$ may be bonded to each other to form a ring. Examples of the ring formed by $A^x$ and $A^y$ include a substituted or unsubstituted unsaturated heterocyclic ring having 4 to 30 carbon atoms, and a substituted or unsubstituted unsaturated carbocyclic ring having 6 to 30 carbon atoms.

The unsaturated heterocyclic ring having 4 to 30 carbon atoms and the unsaturated carbocyclic ring having 6 to 30 carbon atoms are not particularly limited, and may or may not have aromaticity. Examples of the unsaturated heterocyclic ring having 4 to 30 carbon atoms and the unsaturated carbocyclic ring having 6 to 30 carbon atoms are shown below.

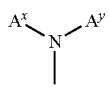

Note that the rings shown below correspond to the above part in the formula (I).

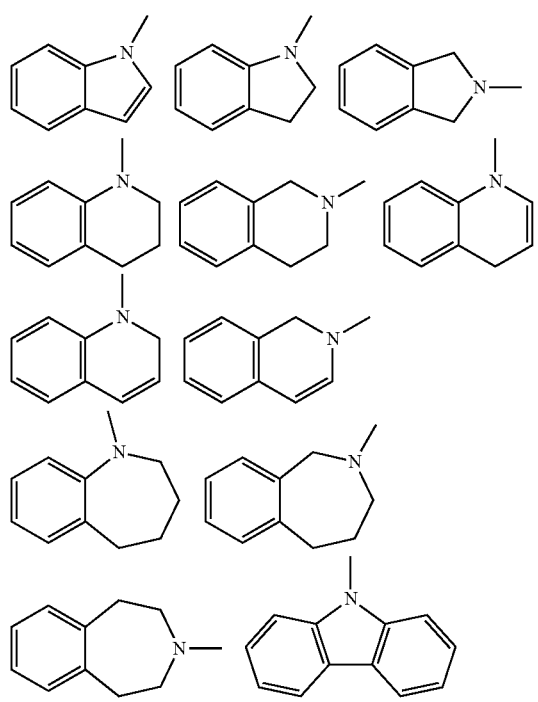

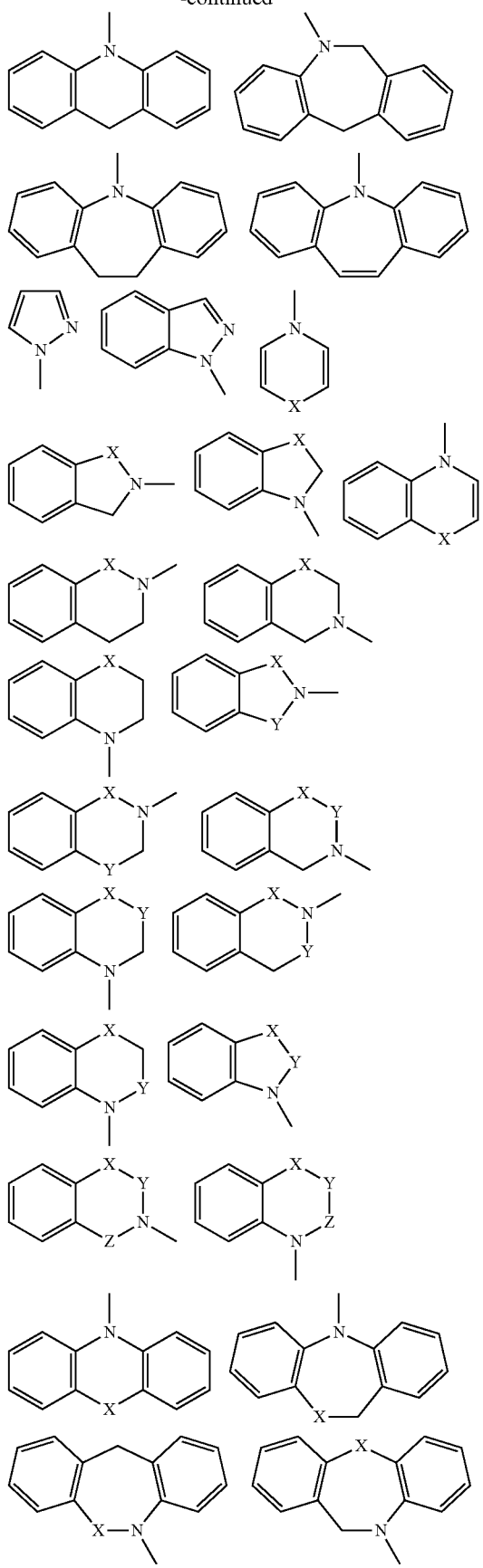

-continued

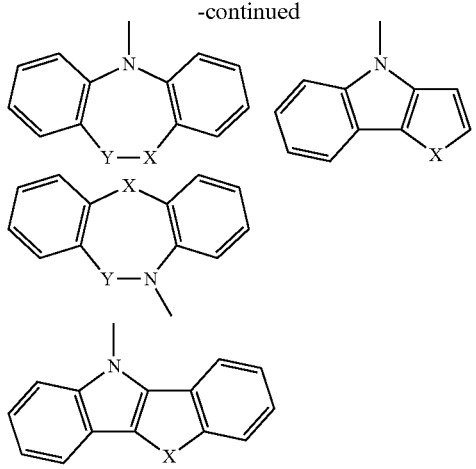

wherein X, Y, and Z are the same as defined above.

These rings may be substituted with a substituent. Examples of the substituent include those mentioned above in connection with a substituent that may substitute the aromatic ring included in $A^x$.

The total number of π electrons included in $A^x$ and $A^y$ is preferably 4 to 24, and more preferably 6 to 18, in order to more advantageously achieve the intended effects of the invention.

Examples of a preferable combination of $A^x$ and $A^y$ include a combination in which $A^x$ is an aromatic hydrocarbon group having 4 to 30 carbon atoms or an aromatic heterocyclic ring group having 4 to 30 carbon atoms, and $A^y$ is a hydrogen atom,
a cycloalkyl group having 3 to 8 carbon atoms, an aromatic hydrocarbon group having 6 to 12 carbon atoms (that is optionally substituted with a halogen atom, a cyano group, an alkyl group having 1 to 6 carbon atoms, an alkoxy group having 1 to 6 carbon atoms, or a cycloalkyl group having 3 to 8 carbon atoms), an aromatic heterocyclic ring group having 3 to 9 carbon atoms (that is optionally substituted with a halogen atom, an alkyl group having 1 to 6 carbon atoms, an alkoxy group having 1 to 6 carbon atoms, or a cyano group), a substituted or unsubstituted alkyl group having 1 to 20 carbon atoms, a substituted or unsubstituted alkenyl group having 1 to 20 carbon atoms, or a substituted or unsubstituted alkynyl group having 2 to 20 carbon atoms, the alkyl group, the alkenyl group, and the alkynyl group being optionally substituted with a halogen atom, a cyano group, an alkoxy group having 1 to 20 carbon atoms, an alkoxy group having 1 to 12 carbon atoms that is substituted with an alkoxy group having 1 to 12 carbon atoms, a phenyl group, a cyclohexyl group, a cyclic ether group having 2 to 12 carbon atoms, an aryloxy group having 6 to 14 carbon atoms, a hydroxyl group, a benzodioxanyl group, or —$SR^{10}$, and a combination in which $A^x$ and $A^y$ form an unsaturated heterocyclic ring or an unsaturated carbocyclic ring. Note that $R^{10}$ is the same as defined above.

Examples of a more preferable combination of $A^x$ and $A^y$ include a combination in which $A^x$ is a group among the groups respectively having the following structures, and $A^y$ is a hydrogen atom, a cycloalkyl group having 3 to 8 carbon atoms, an aromatic hydrocarbon group having 6 to 12 carbon atoms (that is optionally substituted with a halogen atom, a cyano group, an alkyl group having 1 to 6 carbon atoms, an alkoxy group having 1 to 6 carbon atoms, or a cycloalkyl group having 3 to 8 carbon atoms), an aromatic heterocyclic ring group having 3 to 9 carbon atoms (that is optionally substituted with a halogen atom, an alkyl group having 1 to 6 carbon atoms, an alkoxy group having 1 to 6 carbon atoms, or a cyano group), a substituted or unsubstituted alkyl group having 1 to 20 carbon atoms, a substituted or unsubstituted alkenyl group having 1 to 20 carbon atoms, or a substituted or unsubstituted alkynyl group having 2 to 20 carbon atoms, the alkyl group, the alkenyl group, and the alkynyl group being optionally substituted with a halogen atom, a cyano group, an alkoxy group having 1 to 20 carbon atoms, an alkoxy group having 1 to 12 carbon atoms that is substituted with an alkoxy group having 1 to 12 carbon atoms, a phenyl group, a cyclohexyl group, a cyclic ether group having 2 to 12 carbon atoms, an aryloxy group having 6 to 14 carbon atoms, a hydroxyl group, a benzodioxanyl group, or —$SR^{10}$. Note that $R^{10}$ is the same as defined above.

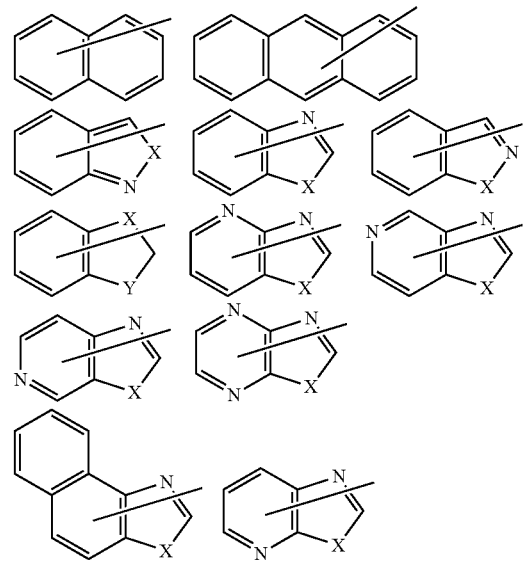

wherein X and Y are the same as defined above.

Examples of a particularly preferable combination of $A^x$ and $A^y$ include a combination in which $A^x$ is a group among the groups respectively having the following structures, and $A^y$ is a hydrogen atom, a cycloalkyl group having 3 to 8 carbon atoms, an aromatic hydrocarbon group having 6 to 12 carbon atoms (that is optionally substituted with a halogen atom, a cyano group, an alkyl group having 1 to 6 carbon atoms, an alkoxy group having 1 to 6 carbon atoms, or a cycloalkyl group having 3 to 8 carbon atoms), an aromatic heterocyclic ring group having 3 to 9 carbon atoms (that is optionally substituted with a halogen atom, an alkyl group having 1 to 6 carbon atoms, an alkoxy group having 1 to 6 carbon atoms, or a cyano group), a substituted or unsubstituted alkyl group having 1 to 20 carbon atoms, a substituted or unsubstituted alkenyl group having 1 to 20 carbon atoms, or a substituted or unsubstituted alkynyl group having 2 to 20 carbon atoms, the alkyl group, the alkenyl group, and the alkynyl group being optionally substituted with a halogen atom, a cyano group, an alkoxy group having 1 to 20 carbon atoms, an alkoxy group having 1 to 12 carbon atoms that is substituted with an alkoxy group having 1 to 12 carbon atoms, a phenyl group, a cyclohexyl group, a cyclic ether group having 2 to 12 carbon atoms, an aryloxy group having 6 to 14 carbon atoms, a hydroxyl group, a benzodioxanyl group, or —SR$^{10}$. Note that X is the same as defined above, and R$^{10}$ is the same as defined above.

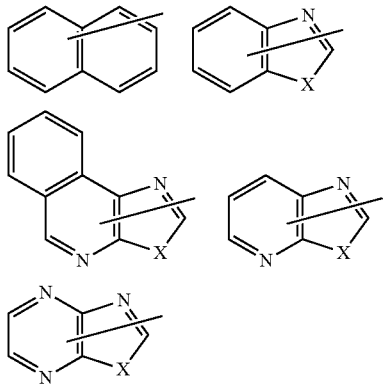

A$^1$ is a substituted or unsubstituted trivalent aromatic group. The trivalent aromatic group may be a trivalent carbocyclic aromatic group, or may be a trivalent heterocyclic aromatic group. It is preferable that the trivalent aromatic group be a trivalent carbocyclic aromatic group, more preferably a trivalent benzene ring group or a trivalent naphthalene ring group, and still more preferably a trivalent benzene ring group or a trivalent naphthalene ring group represented by the following formulas, in order to more advantageously achieve the intended effects of the invention.

Note that the substituents Y$^1$ and Y$^2$ are also included in the following formulas so that the bonding state can be easily understood (Y$^1$ and Y$^2$ are the same as defined above; hereinafter the same).

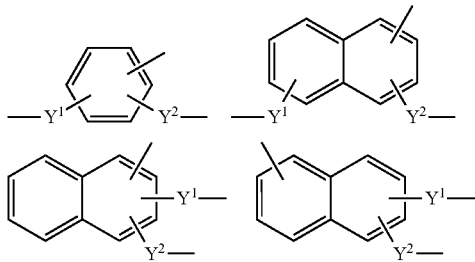

A$^1$ is more preferably a group among the groups respectively represented by the following formulas (A11) to (A25), still more preferably a group among the groups respectively represented by the formulas (A11), (A13), (A15), (A19), and (A23), and particularly preferably the group represented by the formula (A11) or the group represented by the formula (A23).

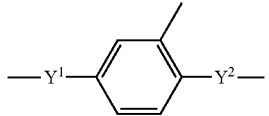
(A11)

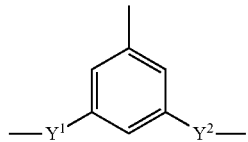
(A12)

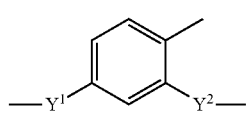
(A13)

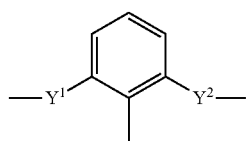
(A14)

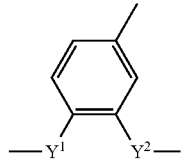
(A15)

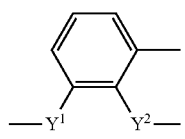
(A16)

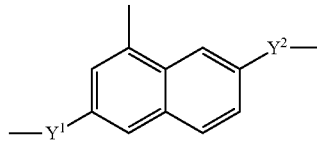
(A17)

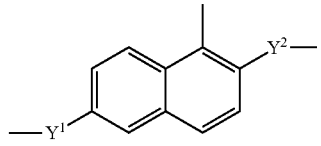
(A18)

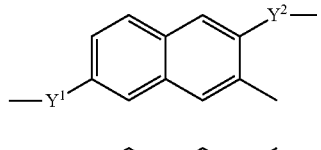
(A19)

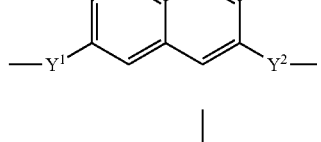
(A20)

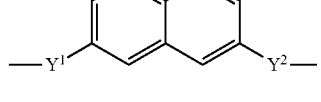
(A21)

-continued

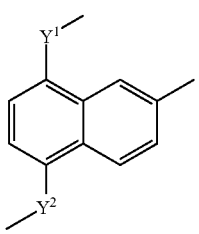
(A22)

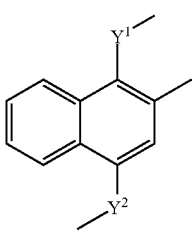
(A23)

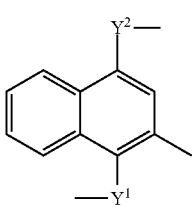
(A24)

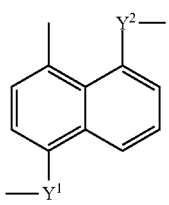
(A25)

Examples of a substituent that may substitute the trivalent aromatic group represented by $A^1$ include those mentioned above in connection with a substituent that may substitute the aromatic ring included in $A^x$. It is preferable that $A^1$ be unsubstituted.

Each of $A^4$ and $A^5$ independently represents a substituted or unsubstituted divalent aromatic group having 6 to 30 carbon atoms.

The aromatic group represented by $A^4$ and $A^5$ may be a monocyclic aromatic group, or may be a polycyclic aromatic group.

Specific examples of a preferable aromatic group represented by $A^4$ and $A^5$ include the groups respectively represented by the following formulas.

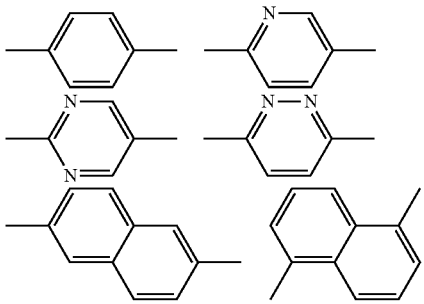

-continued

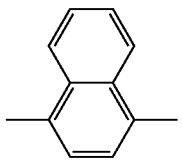

The divalent aromatic group represented by $A^4$ and $A^5$ may be substituted with a substituent at an arbitrary position. Examples of the substituent include a halogen atom, a cyano group, a hydroxyl group, an alkyl group having 1 to 6 carbon atoms, an alkoxy group having 1 to 6 carbon atoms, a nitro group, —C(=O)—OR (wherein R is an alkyl group having 1 to 6 carbon atoms), and the like. Among these, a halogen atom, an alkyl group having 1 to 6 carbon atoms, and an alkoxy group having 1 to 6 carbon atoms are preferable. A fluorine atom is preferable as the halogen atom. A methyl group, an ethyl group, and a propyl group are preferable as the alkyl group having 1 to 6 carbon atoms. A methoxy group and an ethoxy group are preferable as the alkoxy group having 1 to 6 carbon atoms.

It is preferable that each of $A^4$ and $A^5$ independently represent a group among the groups respectively represented by the following formulas (A41), (A42), and (A43) that are optionally substituted with a substituent, and particularly preferably the group represented by the formula (A41) that is optionally substituted with a substituent, in order to more advantageously achieve the intended effects of the invention.

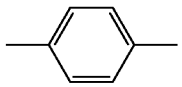
(A41)

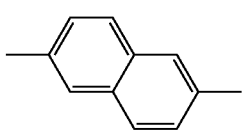
(A42)

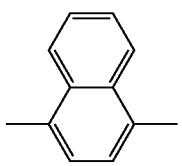
(A43)

$Q^1$ is a hydrogen atom, or a substituted or unsubstituted alkyl group having 1 to 6 carbon atoms.

Examples of the substituted or unsubstituted alkyl group having 1 to 6 carbon atoms include those mentioned above in connection with $A^x$.

$Q^1$ is preferably a hydrogen atom or an alkyl group having 1 to 6 carbon atoms, and more preferably a hydrogen atom or a methyl group.

The polymerizable compound according to one embodiment of the invention may be produced by effecting the following reaction, for example.

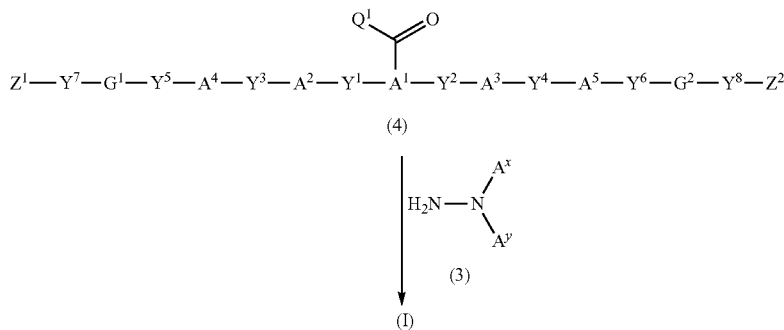

(I)

wherein $Y^1$ to $Y^8$, $G^1$, $G^2$, $Z^1$, $Z^2$, $A^x$, $A^y$, $A^1$ to $A^5$, and $Q^1$ are the same as defined above.

Specifically, the polymerizable compound represented by the formula (I) can be produced with high selectivity in high yield by reacting the hydrazine compound represented by the formula (3) (hydrazine compound (3)) with the carbonyl compound represented by the formula (4) (carbonyl compound (4)) in a molar ratio (hydrazine compound (3): carbonyl compound (4)) of 1:2 to 2:1 (preferably 1:1.5 to 1.5:1).

The above reaction may be effected in the presence of an acid catalyst such as an organic acid (e.g., (±)-10-camphorsulfonic acid or p-toluenesulfonic acid) or an inorganic acid (e.g., hydrochloric acid or sulfuric acid). The addition of the acid catalyst may reduce the reaction time, and improve the yield. The acid catalyst is normally added in an amount of 0.001 to 1 mol based on 1 mol of the carbonyl compound (4). The acid catalyst may be added directly, or a solution prepared by dissolving the acid catalyst in an appropriate solvent may be added.

A solvent used for the above reaction is not particularly limited as long as the solvent is inert to the reaction. Examples of the solvent include an alcohol-based solvent such as methyl alcohol, ethyl alcohol, n-propyl alcohol, isopropyl alcohol, n-butyl alcohol, isobutyl alcohol, sec-butyl alcohol, and t-butyl alcohol; an ether-based solvent such as diethyl ether, tetrahydrofuran, 1,2-dimethoxyethane, 1,4-dioxane, and cyclopentyl methyl ether; an ester-based solvent such as ethyl acetate, propyl acetate, and methyl propionate; an aromatic hydrocarbon-based solvent such as benzene, toluene, and xylene; an aliphatic hydrocarbon-based solvent such as n-pentane, n-hexane, and n-heptane; an amide-based solvent such as N,N-dimethylformamide, N-methylpyrrolidone, and hexamethylphosphoric acid triamide; a sulfur-containing solvent such as dimethyl sulfoxide and sulfolane; a mixed solvent including two or more solvents among these solvents; and the like.

Among these, an alcohol-based solvent, an ether-based solvent, and a mixed solvent including an alcohol-based solvent and an ether-based solvent are preferable.

The solvent may be used in an appropriate amount taking account of the type of each compound, the reaction scale, and the like. The solvent is normally used in an amount of 1 to 100 g per gram of the hydrazine compound (3).

The reaction proceeds smoothly when the reaction temperature is within the range from −10° C. to the boiling point of the solvent. The reaction time is selected taking account of the reaction scale, but is normally several minutes to several hours.

The hydrazine compound (3) may be produced as described below.

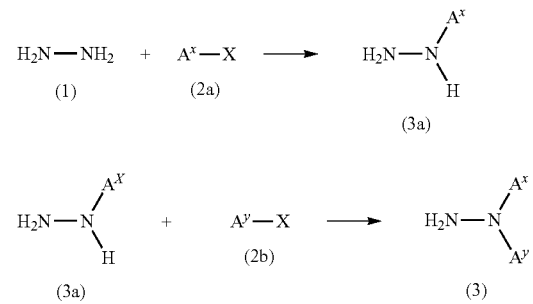

wherein $A^x$ and $A^y$ are the same as defined above, and X is a leaving group (e.g., halogen atom, methanesulfonyloxy group, or p-toluenesulfonyloxy group).

Specifically, the compound represented by the formula (2a) is reacted with the hydrazine (1) in an appropriate solvent in a molar ratio (compound (2a):hydrazine (1)) of 1:1 to 1:20 (preferably 1:2 to 1:10) to obtain the corresponding hydrazine compound (3a), and the hydrazine compound (3a) is reacted with the compound represented by the formula (2b) to obtain the hydrazine compound (3).

Hydrazine monohydrate is normally used as the hydrazine (1). A commercially available product may be used directly as the hydrazine (1).

A solvent used for the above reaction is not particularly limited as long as the solvent is inert to the reaction. Examples of the solvent include an alcohol-based solvent such as methyl alcohol, ethyl alcohol, n-propyl alcohol, isopropyl alcohol, n-butyl alcohol, isobutyl alcohol, sec-butyl alcohol, and t-butyl alcohol; an ether-based solvent such as diethyl ether, tetrahydrofuran, 1,2-dimethoxyethane, 1,4-dioxane, and cyclopentyl methyl ether; an aromatic hydrocarbon-based solvent such as benzene, toluene, and xylene; an aliphatic hydrocarbon-based solvent such as n-pentane, n-hexane, and n-heptane; an amide-based solvent such as N,N-dimethylformamide, N-methylpyrrolidone, and hexamethylphosphoric acid triamide; a sulfur-containing solvent such as dimethyl sulfoxide and sulfolane; a mixed solvent including two or more solvents among these solvents; and the like.

Among these, an alcohol-based solvent, an ether-based solvent, and a mixed solvent including an alcohol-based solvent and an ether-based solvent are preferable.

The solvent may be used in an appropriate amount taking account of the type of each compound, the reaction scale, and the like. The solvent is normally used in an amount of 1 to 100 g per gram of hydrazine.

The reaction proceeds smoothly when the reaction temperature is within the range from −10° C. to the boiling point of the solvent. The reaction time is selected taking account of the reaction scale, but is normally several minutes to several hours.

The hydrazine compound (3) may also be produced by reducing the diazonium salt (5) (see below) using a known method.

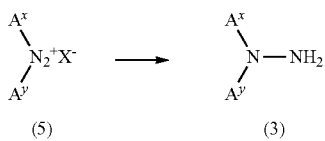

wherein $A^x$ and $A^y$ are the same as defined above, and $X^-$ is an anion that is a counter ion for diazonium. Examples of the anion represented by $X^-$ include an inorganic anion such as a hexafluorophosphoric acid ion, a fluoroboric acid ion, a chloride ion, and a sulfuric acid ion; an organic anion such as a polyfluoroalkylcarboxylic acid ion, a polyfluoroalkylsulfonic acid ion, a tetraphenylboric acid ion, an aromatic carboxylic acid ion, and an aromatic sulfonic acid ion; and the like.

Examples of a reducing agent used for the above reaction include a metal salt reducing agent.

The term "metal salt reducing agent" normally refers to a compound that includes a metal having a small valence, or a compound that includes a metal ion and a hydride source (see "Yuki Gosei Jikkenhou Handbook (Handbook of Organic Synthesis Experiments)", 1990, edited by The Society of Synthetic Organic Chemistry, Japan, published by Maruzen Co., Ltd., p. 810).

Examples of the metal salt reducing agent include $NaAlH_4$, $NaAlH_p(Or)_q$ (wherein each of p and q independently represents an integer from 1 to 3, provided that p+q=4, and r is an alkyl group having 1 to 6 carbon atoms), $LiAlH_4$, $iBu_2AlH$, $LiBH_4$, $NaBH_4$, $SnCl_2$, $CrCl_2$, $TiCl_3$, and the like.

The reduction reaction may be effected under known reaction conditions. For example, the reduction reaction may be effected under the reaction conditions described in JP-A-2005-336103, "Shin-Jikken Kagaku Koza (New Experimental Chemistry Course)", 1978, Vol. 14, published by Maruzen Co., Ltd., "Jikken Kagaku Koza (Experimental Chemistry Course)", 1992, Vol. 20, published by Maruzen Co., Ltd., or the like.

The diazonium salt (5) may be produced from aniline or the like using a known method.

The carbonyl compound (4) may be produced by appropriately bonding and modifying a plurality of known compounds having the desired structure by arbitrarily combining an ether linkage (—O—)—forming reaction, an ester linkage (—C(═O)—O— or —O—C(═O)—)—forming reaction, a carbonate linkage (—O—C(═O)—O—)—forming reaction, and an amide linkage (—C(═O)—NH— or —NH—C(═O)—)—forming reaction.

An ether linkage may be formed as described below.

(i) A compound represented by D1-hal (wherein hal is a halogen atom; hereinafter the same) and a compound represented by D2-OMet (wherein Met is an alkali metal (mainly sodium); hereinafter the same) are mixed and condensed (Williamson synthesis). Note that D1 and D2 are an arbitrary organic group (hereinafter the same).

(ii) A compound represented by D1-hal and a compound represented by D2-OH are mixed and condensed in the presence of a base (e.g., sodium hydroxide or potassium hydroxide).

(iii) A compound represented by D1-J (wherein J is an epoxy group) and a compound represented by D2-OH are mixed and condensed in the presence of a bas(e.g., sodium hydroxide or potassium hydroxide).

(iv) A compound represented by D1-OFN (wherein OFN is a group that includes an unsaturated bond) and a compound represented by D2-OMet are mixed and subjected to an addition reaction in the presence of a base (e.g., sodium hydroxide or potassium hydroxide).

(v) A compound represented by D1-hal and a compound represented by D2-OMet are mixed and condensed in the presence of copper or cuprous chloride (Ullmann condensation).

An ester linkage and an amide linkage may be formed as described below.

(vi) A compound represented by D1-COOH and a compound represented by D2-OH or $D2-NH_2$ are subjected to dehydration and condensation in the presence of a dehydration-condensation agent (e.g., N,N-dicyclohexylcarbodiimide).

(vii) A compound represented by D1-COOH is reacted with a halogenating agent to obtain a compound represented by D1-CO-hal, and the compound represented by D1-CO-hal is reacted with a compound represented by D2-OH or $D2-NH_2$ in the presence of a base.

(viii) A compound represented by D1-COOH is reacted with an acid anhydride to obtain a mixed acid anhydride, and the mixed acid anhydride is reacted with a compound represented by D2-OH or $D2-NH_2$.

(ix) A compound represented by D1-COOH and a compound represented by D2-OH or $D2-NH_2$ are subjected to dehydration and condensation in the presence of an acid catalyst or a base catalyst.

More specifically, the carbonyl compound (4) may be produced using the following method (see the following reaction formula).

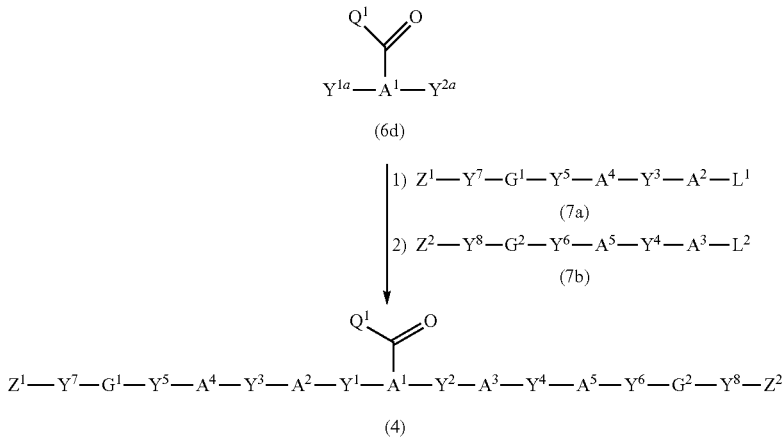

wherein $Y^1$ to $Y^8$, $G^1$, $G^2$, $Z^1$, $Z^2$, $A^1$ to $A^5$, and $Q^1$ are the same as defined above, $L^1$ and $L^2$ are a leaving group (e.g., hydroxyl group, halogen atom, methanesulfonyloxy group, or p-toluenesulfonyloxy group), $—Y^{1a}$ is a group that reacts with $-L^1$ to form $—Y^1—$, and $—Y^{2a}$ is a group that reacts with $-L^2$ to form $—Y^2—$.

Specifically, the carbonyl compound (4) according to one embodiment of the invention may be produced by sequentially reacting the compound represented by the formula (7a) and the compound represented by the formula (7b) with the compound represented by the formula (6d) using an ether linkage (—O—)—forming reaction, an ester linkage (—C(=O)—O— or —O—C(=O)—)—forming reaction, or a carbonate linkage (—O—C(=O)—O—)—forming reaction known in the art.

The carbonyl compound (4') wherein Y' is a group represented by $Y^{11}$—C(=O)—O—, and the group represented by $Z^2$—$Y^8$-$G^2$-$Y^6$-$A^5$-$Y^4$-$A^3$-$Y^2$— is identical with the group represented by $Z^1$—$Y^7$-$G^1$-$Y^5$-$A^4$-$Y^3$-$A^2$-$Y^1$—(hereinafter referred to as "compound (4')") may be produced as shown below.

ratio (compound (6):compound (7)) of 1:2 to 1:4 (preferably 1:2 to 1:3) to produce the target compound (4') with high selectivity in high yield.

When the compound (7) is a compound (carboxylic acid) represented by the formula (7) wherein $L^1$ is a hydroxyl group, the target product may be obtained by effecting the reaction in the presence of a dehydration-condensation agent (e.g., 1-ethyl-3-(3-dimethylaminopropyl)carbodiimide hydrochloride or dicyclohexylcarbodiimide).

The dehydration-condensation agent is normally used in an amount of 1 to 3 mol based on 1 mol of the compound (7).

When the compound (7) is a compound (carboxylic acid) represented by the formula (7) wherein $L^1$ is a hydroxyl group, the target product may also be obtained by effecting the reaction in the presence of a sulfonyl halide (e.g., methanesulfonyl chloride or p-toluenesulfonyl chloride) and a base (e.g., triethylamine, diisopropylethylamine, pyridine, or 4-(dimethylamino)pyridine).

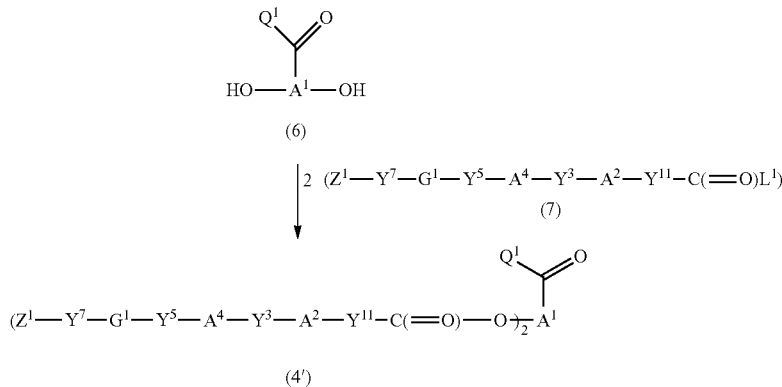

wherein $Y^3$, $Y^5$, $Y^7$, $G^1$, $Z^1$, $A^1$, $A^2$, $A^4$, $Q^1$, $A^4$, $Q^1$, and $L^1$ are the same as defined above, $Y^{11}$ is a group whereby $Y^1$ is represented by $Y^{11}$—C(=O)—O—, and $Y^1$ is the same as defined above.

Specifically, the dihydroxy compound represented by the formula (6) (compound (6)) is reacted with the compound represented by the formula (7) (compound (7)) in a molar The sulfonyl halide is normally used in an amount of 1 to 3 mol based on 1 mol of the compound (7).

The base is normally used in an amount of 1 to 3 mol based on 1 mol of the compound (7).

In this case, a compound (mixed acid anhydride) represented by the formula (7) wherein $L^1$ is a sulfonyloxy group may be isolated, and subjected to the subsequent reaction.

When the compound (7) is a compound (acid halide) represented by the formula (7) wherein $L^1$ is a halogen atom, the target product may be obtained by effecting the reaction in the presence of a base.

Examples of the base include an organic base such as triethylamine and pyridine; and an inorganic base such as sodium hydroxide, sodium carbonate, and sodium hydrogen carbonate.

The base is normally used in an amount of 1 to 3 mol based on 1 mol of the compound (7).

Examples of a solvent used for the above reaction include a chlorine-based solvent such as chloroform and methylene chloride; an amide-based solvent such as N-methylpyrrolidone, N,N-dimethylformamide, N,N-dimethylacetamide, and hexamethylphosphoric acid triamide; an ether-based solvent such as 1,4-dioxane, cyclopentyl methyl ether, tetrahydrofuran, tetrahydropyran, and 1,3-dioxolane; a sulfur-containing solvent such as dimethyl sulfoxide and sulfolane; an aromatic hydrocarbon-based solvent such as benzene, toluene, and xylene; an aliphatic hydrocarbon-based solvent such as n-pentane, n-hexane, and n-octane; an alicyclic hydrocarbon-based solvent such as cyclopentane and cyclohexane; a mixed solvent including two or more solvents among these solvents; and the like.

The solvent may be used in an appropriate amount taking account of the type of each compound, the reaction scale, and the like. The solvent is normally used in an amount of 1 to 50 g per gram of the hydroxy compound (6).

Many of the compounds (6) are known compounds, and may be produced using a known method.

For example, the compound (6) may be produced using the following method (see the following reaction formula) (see WO2009/042544 and The Journal of Organic Chemistry, 2011, 76, 8082-8087). A commercially available product may be used as the compound (6) either directly or after purification.

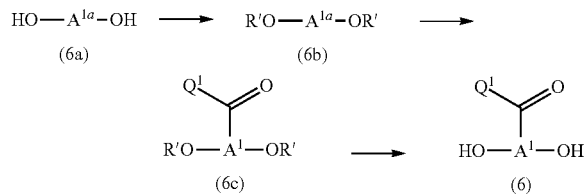

wherein $A^1$ and $Q^1$ are the same as defined above, $A^{1a}$ is a divalent aromatic group that forms $A^1$ through formylation or acylation, and R' is a protecting group for a hydroxyl group, such as an alkyl group having 1 to 6 carbon atoms (e.g., methyl group or ethyl group), or an alkoxyalkyl group having 2 to 6 carbon atoms (e.g., methoxymethyl group).

Specifically, the target compound (6) may be produced by alkylating the hydroxyl groups of the dihydroxy compound represented by the formula (6a) (e.g., 1,4-dihydroxybenzene or 1,4-dihydroxynaphthalene) to obtain the compound represented by the formula (6b), effecting formylation or acylation at the ortho position with respect to the OR' group using a known method to obtain the compound represented by the formula (6c), and deprotecting (dealkylating) the compound represented by the formula (6c).

A commercially available product may be used as the compound (6) either directly or after purification.

Most of the compounds (7) are known compounds. The carbonyl compound (7) may be produced by appropriately bonding and modifying a plurality of known compounds having a desired structure by arbitrarily combining an ether linkage (—O—)—forming reaction, an ester linkage (—C(=O)—O— or —O—C(=O)—)—forming reaction, a carbonate linkage (—O—C(=O)—O—)—forming reaction, and an amide linkage (—C(=O)—NH— or —NH—C(=O)—)—forming reaction.

For example, when the compound (7) is a compound represented by the following formula (7') (compound (7')), the compound (7) may be produced as shown below using a dicarboxylic acid represented by the formula (9') (compound (9')).

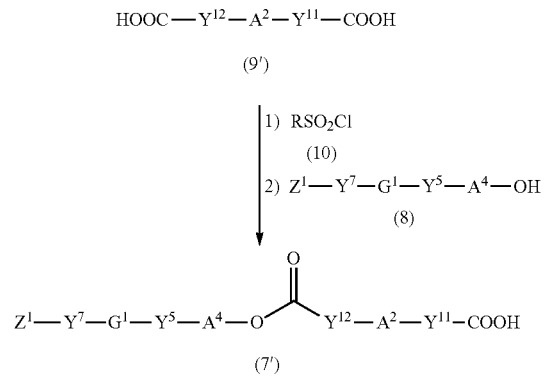

wherein $Y^5$, $Y^7$, $G^1$, $Z^1$, $A^2$, $A^4$, and $Y^{12}$ are the same as defined above, $Y^3$ is a group whereby $Y^3$ is represented by —O—C(=O)—$Y^{12}$, and R is an alkyl group such as a methyl group or an ethyl group, or a substituted or unsubstituted aryl group such as a phenyl group or a p-methylphenyl group.

Specifically, the sulfonyl chloride represented by the formula (10) is reacted with the compound (9') in the presence of a base (e.g., triethylamine or 4-(dimethylamino)pyridine).

The compound (8) and a base (e.g., triethylamine or 4-(dimethylamino)pyridine) are added to the reaction mixture to effect a reaction.

Sulfonyl chloride is normally used in an amount of 0.5 to 0.7 equivalents based on 1 equivalent of the compound (9').

The compound (8) is normally used in an amount of 0.5 to 0.6 equivalents based on 1 equivalent of the compound (9').

The base is normally used in an amount of 0.5 to 0.7 equivalents based on 1 equivalent of the compound (9').

The reaction temperature is 20 to 30° C. The reaction time is selected taking account of the reaction scale and the like, but is normally several minutes to several hours.

Examples of a solvent used for the above reaction include those mentioned above in connection with the solvent that may be used when producing the compound (4'). It is preferable to use an ether as the solvent.

The solvent may be used in an appropriate amount taking account of the type of each compound, the reaction scale, and the like. The solvent is normally used in an amount of 1 to 50 g per gram of the compound (9').

The target product is isolated by performing a post-treatment operation normally employed in synthetic organic chemistry after completion of the reaction, optionally followed by a known purification/separation means such as column chromatography, recrystallization, or distillation.

The structure of the target product may be identified by measurement/elemental analysis (e.g., NMR spectrometry, IR spectrometry, or mass spectrometry), and the like.

The polymerizable compound according to one embodiment of the invention is useful as a raw material for producing the polymer and the optically anisotropic article according to the embodiments of the invention (described below), and is particularly useful as a raw material for producing a polymer having reverse wavelength dispersion. Specifically, when producing a copolymer using the polymerizable compound according to one embodiment of the invention and a monomer that is copolymerizable with the polymerizable compound according to one embodiment of the invention, it is possible to produce a copolymer having reverse wavelength dispersion by copolymerizing the polymerizable compound according to one embodiment of the invention with a monomer that produces a polymer that has reverse wavelength dispersion when polymerized. In this case, since the drying temperature employed when forming a liquid crystal layer can be reduced while maintaining the reverse wavelength dispersion, it is possible to improve the energy efficiency, and reduce the cost required to produce a liquid crystal polymer film.

2) Polymerizable Composition

A polymerizable composition according to one embodiment of the invention includes the polymerizable compound according to one embodiment of the invention, and an initiator. The initiator is used to more efficiently polymerize the polymerizable compound according to one embodiment of the invention.

The initiator may be appropriately selected taking account of the type of the polymerizable group included in the polymerizable compound. For example, a radical initiator may be used when the polymerizable group is a radically polymerizable group, an anionic initiator may be used when the polymerizable group is an anionically polymerizable group, and a cationic initiator may be used when the polymerizable group is a cationically polymerizable group.

Examples of the radical initiator include a thermal radical generator (compound) that generates active species that initiate the polymerization of the polymerizable compound upon heating, and a photo-radical generator (compound) that generates active species that initiate the polymerization of the polymerizable compound upon exposure to exposure light (e.g., visible rays, ultraviolet rays (e.g., i-line), deep ultraviolet rays, electron beams, or X-rays). It is preferable to use the photo-radical generator.

Examples of the photo-radical generator include an acetophenone-based compound, a biimidazole-based compound, a triazine-based compound, an O-acyloxime-based compound, an onium salt-based compound, a benzoin-based compound, a benzophenone-based compound, an α-diketone-based compound, a polynuclear quinone-based compound, a xanthone-based compound, a diazo-based compound, an imidosulfonate-based compound, and the like. These compounds generate either or both of active radicals and an active acid upon exposure. These photo-radical generators may be used either alone or in combination.

Specific examples of the acetophenone-based compound include
2-hydroxy-2-methyl-1-phenylpropan-1-one,
2-methyl-1-[4-(methylthio)phenyl]-2-morpholinopropan-1-one,
2-benzyl-2-dimethylamino-1-(4-morpholinophenyl)butan-1-one, 1-hydroxycyclohexyl phenyl ketone, 2,2-dimethoxy-1,2-diphenylethan-1-one, 1,2-octanedione,
2-benzyl-2-dimethylamino-4'-morpholinobutyrophenone, and the like.

Specific examples of the biimidazole-based compound include 2,2'-bis(2-chlorophenyl)-4,4',5,5'-tetrakis(4-ethoxycarbonylphenyl)-1,2'-biimidazole,
2,2'-bis(2-bromophenyl)-4,4',5,5'-tetrakis(4-ethoxycarbonylphenyl)-1,2'-biimidazole,
2,2'-bis(2-chlorophenyl)-4,4',5,5'-tetraphenyl-1,2'-biimidazole,
2,2'-bis(2,4-dichlorophenyl)-4,4',5,5'-tetraphenyl-1,2'-biimidazole,
2,2'-bis(2,4,6-trichlorophenyl)-4,4',5,5'-tetraphenyl-1,2'-biimidazole,
2,2'-bis(2-bromophenyl)-4,4',5,5'-tetraphenyl-1,2'-biimidazole,
2,2'-bis(2,4-dibromophenyl)-4,4',5,5'-tetraphenyl-1,2'-biimidazole,
2,2'-bis(2,4,6-tribromophenyl)-4,4',5,5'-tetraphenyl-1,2'-biimidazole, and the like.

When using a biimidazole-based compound as a photoinitiator, it is preferable to use a hydrogen donor in combination with the biimidazole-based compound in order to further improve sensitivity.

The term "hydrogen donor" used herein refers to a compound that can donate a hydrogen atom to radicals generated by the biimidazole-based compound upon exposure. A mercaptan-based compound, an amine-based compound, and the like are preferable as the hydrogen donor.

Examples of the mercaptan-based compound include 2-mercaptobenzothiazole, 2-mercaptobenzoxazole, 2-mercaptobenzimidazole, 2,5-dimercapto-1,3,4-thiadiazole, 2-mercapto-2,5-dimethylaminopyridine, and the like. Examples of the amine-based compound include 4,4'-bis(dimethylamino)benzophenone, 4,4'-bis(diethylamino)benzophenone, 4-diethylaminoacetophenone, 4-dimethylaminopropiophenone, ethyl-4-dimethylaminobenzoate, 4-dimethylaminobenzoic acid, 4-dimethylaminobenzonitrile, and the like.

Specific examples of the triazine-based compound include a triazine-based compound that includes a halomethyl group, such as
2,4,6-tris(trichloromethyl)-s-triazine, 2-methyl-4,6-bis(trichloromethyl)-s-triazine,
2-[2-(5-methylfuran-2-yl)ethenyl]-4,6-bis(trichloromethyl)-s-triazine,
2-[2-(furan-2-yl)ethenyl]-4,6-bis(trichloromethyl)-s-triazine,
2-[2-(4-diethylamino-2-methylphenyl)ethenyl]-4,6-bis(trichloromethyl)-s-triazine,
2-[2-(3,4-dimethoxyphenyl)ethenyl]-4,6-bis(trichloromethyl)-s-triazine,
2-(4-methoxyphenyl)-4, 6-bis(trichloromethyl)-s-triazine,
2-(4-ethoxystyryl)-4,6-bis(trichloromethyl)-s-triazine, and
2-(4-n-butoxyphenyl)-4,6-bis(trichloromethyl)-s-triazine.

Specific examples of the O-acyloxime-based compound include
1-[4-(phenylthio)phenyl]-heptane-1,2-dione-2-(O-benzoyloxime),
1-[4-(phenylthio)phenyl]-octane-1,2-dione-2-(O-benzoyloxime),
1-[4-(benzoyl)phenyl]-octane-1,2-dione-2-(O-benzoyloxime),
1-[9-ethyl-6-(2-methylbenzoyl)-9H-carbazol-3-yl]-ethanone -1-(O-acetyloxime),
1-[9-ethyl-6-(3-methylbenzoyl)-9H-carbazol-3-yl]-ethanone -1-(O-acetyloxime),
1-(9-ethyl-6-benzoyl-9H-carbazol-3-yl)-ethanone-1-(O-acetyloxime),
ethanone-1-[9-ethyl-6-(2-methyl-4-tetrahydrofuranylbenzoyl)-9H-carbazol-3-yl]-1-(O-acetyloxime), ethanone-1-[9-ethyl-6-(2-methyl-4-tetrahydropyranylbenzoyl)-9H-carbazol-3-yl]-1-(O-acetyloxime),
ethanone-1-[9-ethyl-6-(2-methyl-5-tetrahydrofuranylbenzoyl)-9H-carbazol-3-yl]-1-(O-acetyloxime),
ethanone-1-[9-ethyl-6-(2-methyl-5-tetrahydropyranylbenzoyl)-9H-carbazol-3-yl]-1-(O-acetyloxime),
ethanone-1-[9-ethyl-6-{2-methyl-4-(2,2-dimethyl-1,3-dioxolanyl)benzoyl}-9H-carbazol-3-yl]-1-(O-acetyloxime),
ethanone-1-[9-ethyl-6-(2-methyl-4-tetrahydrofuranyl-methoxybenzoyl) -9H-carbazol-3-yl]-1-(O-acetyloxime),
ethanone-1-[9-ethyl-6-(2-methyl-4-tetrahydropyranyl-methoxybenzoyl) -9H-carbazol-3-yl]-1-(O-acetyloxime),
ethanone-1-[9-ethyl-6-(2-methyl-5-tetrahydrofuranyl-methoxybenzoyl) -9H-carbazol-3-yl]-1-(O-acetyloxime),
ethanone-1-[9-ethyl-6-(2-methylbenzoyl)-9H-carbazol-3-yl]-1-(O-acetyloxime),
ethanone-1-[9-ethyl-6-(2-methyl-5-tetrahydropyranyl-methoxybenzoyl) -9H-carbazol-3-yl]-1-(O-acetyloxime),
ethanone-1-[9-ethyl-6-{2-methyl-4-(2,2-dimethyl-1,3-dioxolanyl)methoxybenzoyl}-9H-carbazol-3-yl]-1-(O-acetyloxime), and the like.

A commercially available product may be used directly as the photo-radical generator. Specific examples of a commercially available product that may be used as the photo-radical generator include Irgacure 907, Irgacure 184, Irgacure 369, Irgacure 651, Irgacure 819, Irgacure 907, and Irgacure OXE02 (manufactured by BASF); Adekaoptomer N1919 (manufactured by Adeka Corporation); and the like.

Examples of the anionic initiator include an alkyllithium compound; a monolithium salt or a monosodium salt of biphenyl, naphthalene, pyrene, and the like; a polyfunctional initiator such as a dilithium salt and a trilithium salt; and the like.

Examples of the cationic initiator include a proton acid such as sulfuric acid, phosphoric acid, perchloric acid, and trifluoromethanesulfonic acid; a Lewis acid such as boron trifluoride, aluminum chloride, titanium tetrachloride, and tin tetrachloride; an aromatic onium salt or a combination of an aromatic onium salt and a reducing agent; and the like.

These initiators may be used either alone or in combination.

The polymerizable composition according to one embodiment of the invention normally includes the initiator in an amount of 0.1 to 30 parts by weight, and preferably 0.5 to 10 parts by weight, based on 100 parts by weight of the polymerizable compound.

It is preferable to add a surfactant to the polymerizable composition according to one embodiment of the invention in order to adjust the surface tension of the polymerizable composition. The surfactant is not particularly limited, but is preferably a nonionic surfactant. A commercially available product may be used as the nonionic surfactant. Examples of a commercially available product that may be used as the nonionic surfactant include an oligomer having a molecular weight of about several thousand (e.g., "KH-40" manufactured by AGC Seimi Chemical Co., Ltd.), and the like. The surfactant is normally added to the polymerizable composition according to one embodiment of the invention in an amount of 0.01 to 10 parts by weight, and preferably 0.1 to 2 parts by weight, based on 100 parts by weight of the polymerizable compound.

The polymerizable composition according to one embodiment of the invention may further include an additional additive such as an additional copolymerizable monomer, a metal, a metal complex, a dye, a pigment, a fluorescent material, a phosphorescent material, a leveling agent, a thixotropic agent, a gelling agent, a polysaccharide, a UV absorber, an IR (infrared) absorber, an antioxidant, an ion-exchange resin, and a metal oxide (e.g., titanium oxide). Each additional additive is normally added to the polymerizable composition according to one embodiment of the invention in an amount of 0.1 to 20 parts by weight based on 100 parts by weight of the polymerizable compound.

The polymerizable composition according to one embodiment of the invention may be prepared by mixing and dissolving given amounts of the polymerizable compound according to one embodiment of the invention, the initiator, and an optional additive in an appropriate organic solvent.

Examples of the organic solvent include a ketone such as cyclopentanone, cyclohexanone, and methyl ethyl ketone; an acetate such as butyl acetate and amyl acetate; a halogenated hydrocarbon such as chloroform, dichloromethane, and dichloroethane; an ether such as 1,4-dioxane, cyclopentyl methyl ether, tetrahydrofuran, tetrahydropyran, and 1,3-dioxolane; and the like.

The polymerizable composition thus obtained is useful as a raw material for producing the polymer and the optically anisotropic article according to the embodiments of the invention (described below).

3) Polymer

A polymer according to one embodiment of the invention is (1) a polymer obtained by polymerizing the polymerizable compound according to one embodiment of the invention, or (2) a polymer obtained by polymerizing the polymerizable composition according to one embodiment of the invention.

The term "polymerization" used herein refers to a chemical reaction in a broad sense including a normal polymerization reaction and a crosslinking reaction.

(1) Polymer Obtained by Polymerizing Polymerizable Compound

The polymer obtained by polymerizing the polymerizable compound according to one embodiment of the invention may be a homopolymer of the polymerizable compound according to one embodiment of the invention, a copolymer of two or more types of the polymerizable compound according to one embodiment of the invention, or a copolymer of the polymerizable compound according to one embodiment of the invention and an additional copolymerizable monomer.

Examples of the additional copolymerizable monomer include a commercially available product such as LC-242 (manufactured by BASF), the compounds disclosed in JP-A-2007-002208, JP-A-2009-173893, JP-A-2009-274984, JP-A-2010-030979, JP-A-2010-031223, JP-A-2011-006360, PCT/JP2012/060011 (WO2012/141245), PCT/JP2012/061321 (WO2012/147904), PCT/JP2012/064111 (WO2012/169424), PCT/JP2012/065202 (WO2012/176679), and PCT2012/067906, and the like.

Further examples of the additional copolymerizable monomer include
4'-methoxyphenyl 4-(2-methacryloyloxyethyloxy)benzoate, biphenyl
4-(6-methacryloyloxyhexyloxy)benzoate, 4'-cyanobiphenyl
4-(2-acryloyloxyethyloxy)benzoate, 4'-cyanobiphenyl
4-(2-methacryloyloxyethyloxy)benzoate, 3',4'-difluorophenyl
4-(2-methacryloyloxyethyloxy)benzoate, naphthyl
4-(2-methacryloyloxyethyloxy)benzoate, 4-acryloyloxy-4'-decylbiphenyl,
4-acryloyloxy-4'-cyanobiphenyl, 4-(2-acryloyloxyethyloxy)-4'-cyanobiphenyl,
4-(2-methacryloyloxyethyloxy)-4'-methoxybiphenyl, 4-(2-methacryloyloxyethyloxy)-4'-(4"-fluorobenzyloxy)-biphenyl, 4-acryloyloxy-4'-propylcyclohexylphenyl, 4-methacryloyl-4'-butylbicyclohexyl, 4-acryloyl-4'-amyltolane, 4-acryloyl-4'-(3,4-difluorophenyl) bicyclohexyl, (4-amylphenyl) 4-(2-acryloyloxyethyl)benzoate, (4-(4'-propylcyclohexyl)phenyl)

4-(2-acryloyloxyethyl)benzoate, and the like.

A polyfunctional monomer that includes a plurality of polymerizable unsaturated groups (e.g., acryloyl group, methacryloyl group, vinyl group, and allyl group) may also be used as the additional copolymerizable monomer.

Examples of such a polyfunctional monomer include an alkanediol diacrylate such as 1,2-butanediol diacrylate, 1,3-butanediol diacrylate, 1,4-butanediol diacrylate, neopentanediol diacrylate, and 1,6-hexanediol diacrylate; an alkanediol dimethacrylate such as 1,2-butanediol dimethacrylate, 1,3-butanediol dimethacrylate, 1,4-butanediol dimethacrylate, neopentanediol dimethacrylate, and 1,6-hexanediol dimethacrylate; a polyethylene glycol diacrylate such as ethylene glycol diacrylate, diethylene glycol diacrylate, triethylene glycol diacrylate, and tetraethylene glycol diacrylate; a polypropylene glycol diacrylate such as propylene glycol diacrylate, dipropylene glycol diacrylate, tripropylene glycol diacrylate, and tetrapropylene glycol diacrylate; a polyethylene glycol dimethacrylate such as ethylene glycol dimethacrylate, diethylene glycol dimethacrylate, triethylene glycol dimethacrylate, and tetraethylene glycol dimethacrylate; a polypropylene glycol dimethacrylate such as propylene glycol dimethacrylate, dipropylene glycol dimethacrylate, tripropylene glycol dimethacrylate, and tetrapropylene glycol dimethacrylate; a polyethylene glycol divinyl ether such as ethylene glycol divinyl ether, diethylene glycol divinyl ether, triethylene glycol divinyl ether, and tetraethylene glycol divinyl ether; a polyethylene glycol diallyl ether such as ethylene glycol diallyl ether, diethylene glycol diallyl ether, triethylene glycol diallyl ether, and tetraethylene glycol diallyl ether; bisphenol F ethoxylate diacrylate; bisphenol F ethoxylate dimethacrylate; bisphenol A ethoxylate diacrylate; bisphenol A ethoxylate dimethacrylate; trimethylolpropane triacrylate; trimethylolpropane trimethacrylate; trimethylolpropane ethoxylate triacrylate; trimethylolpropane ethoxylate trimethacrylate; trimethylolpropane propoxylate triacrylate; trimethylolpropane propoxylate trimethacrylate; isocyanuric acid ethoxylate triacrylate; glycerol ethoxylate triacrylate; glycerol propoxylate triacrylate; pentaerythritol ethoxylate tetraacrylate; ditrimethylolpropane ethoxylate tetraacrylate; dipentaerythritol ethoxylate hexacrylate; and the like.

The polymerizable compound according to one embodiment of the invention may be (co)polymerized optionally together with the additional copolymerizable monomer in the presence of an appropriate initiator. The initiator may be used in an amount similar to that of the initiator included in the polymerizable composition.

When the polymer according to one embodiment of the invention is a copolymer of the polymerizable compound according to one embodiment of the invention and the additional copolymerizable monomer, the content of constituent units derived from the polymerizable compound according to one embodiment of the invention is not particularly limited, but is preferably 0.1 to 50 wt %, and more preferably 1 to 40 wt %, based on the total constituent units. When the content of structural units derived from the polymerizable compound is within the above range, a polymer that has a high glass transition temperature (Tg) and high hardness can be obtained.

The polymer (1) may be produced by (A) (co)polymerizing the polymerizable compound optionally together with the additional copolymerizable monomer in an appropriate organic solvent in the presence of an appropriate initiator, isolating the target polymer, dissolving the polymer in an appropriate organic solvent to prepare a solution, applying the solution to an appropriate substrate to obtain a film, and drying the film, followed by optional heating, or (B) applying a solution prepared by dissolving the polymerizable compound and an initiator in an organic solvent optionally together with the additional copolymerizable monomer to a substrate using a known coating method, removing the solvent, and effecting polymerization by applying heat or activated energy rays, for example.

Examples of the initiator include those mentioned above in connection with the initiator included in the polymerizable composition.

The organic solvent used for polymerization when implementing the method (A) is not particularly limited as long as the organic solvent is inert. Examples of the organic solvent include an aromatic hydrocarbon such as toluene, xylene, and mesitylene; a ketone such as cyclohexanone, cyclopentanone, and methyl ethyl ketone; an acetate such as butyl acetate and amyl acetate; a halogenated hydrocarbon such as chloroform, dichloromethane, and dichloroethane; an ether such as cyclopentyl methyl ether, tetrahydrofuran, and tetrahydropyran; and the like. Among these, a compound having a boiling point of 60 to 250° C. is preferable, and a compound having a boiling point of 60 to 150° C. is more preferable, from the viewpoint of handling capability.

Examples of the organic solvent used to dissolve the polymer when implementing the method (A), and the organic solvent used for the method (B), include a ketone-based solvent such as acetone, methyl ethyl ketone, methyl isobutyl ketone, cyclopentanone, and cyclohexanone; an ester-based solvent such as butyl acetate and amyl acetate; a halogenated hydrocarbon-based solvent such as dichloromethane, chloroform, and dichloroethane; an ether-based solvent such as tetrahydrofuran, tetrahydropyran, 1,2-dimethoxyethane, 1,4-dioxane, cyclopentyl methyl ether, 1,3-dioxolane; an aprotic polar solvent such as N,N-dimethylformamide, N,N-dimethylacetamide, dimethyl sulfoxide, gamma-butyrolactone, and N-methylpyrrolidone; and the like. Among these, a compound having a boiling point of 60 to 200° C. is preferable from the viewpoint of handling capability. These solvents may be used either alone or in combination.

A substrate formed of a known organic or inorganic material may be used as the substrate. Examples of the organic material include a polycycloolefin (e.g., Zeonex and Zeonor (registered trademark; manufactured by Zeon Corporation); Arton (registered trademark; manufactured by JSR Corporation); and Apel (registered trademark; manufactured by Mitsui Chemicals Inc.)), polyethylene terephthalate, a polycarbonate, a polyimide, a polyamide, polymethyl methacrylate, polystyrene, polyvinyl chloride, polytetrafluoroethylene, cellulose, cellulose triacetate, polyethersulfone, and the like. Examples of the inorganic material include silicon, glass, calcite, and the like. It is preferable to use a substrate formed of an organic material.

The substrate may be a single-layer substrate, or may be a laminate.

The substrate is preferably a substrate formed of an organic material, and more preferably a resin film that is formed of the organic material.

The polymer solution (method (A)) or the solution subjected to polymerization (method (B)) may be applied to the substrate using a known coating method. Examples of the coating method include a curtain coating method, an extrusion coating method, a roll coating method, a spin coating method, a dip coating method, a bar coating method, a spray coating method, a slide coating method, a print coating method, and the like.

(2) Polymer Obtained by Polymerizing Polymerizable Composition

The polymer according to one embodiment of the invention can be easily obtained by polymerizing the polymerizable composition according to one embodiment of the invention. It is preferable to use the polymerizable composition that includes the initiator (particularly a photoinitiator) in order to more efficiently effect polymerization.

Specifically, it is preferable to produce the polymer according to one embodiment of the invention using the method (B) that applies the polymerizable composition according to one embodiment of the invention to a substrate, and polymerizes the applied polymerizable composition. Examples of the substrate include a substrate used to produce an optically anisotropic article (described later), and the like.

The polymerizable composition according to one embodiment of the invention may be applied to the substrate using a known coating method (e.g., bar coating method, spin coating method, roll coating method, gravure coating method, spray coating method, die coating method, cap coating method, or dipping method). A known organic solvent may be added to the polymerizable composition according to one embodiment of the invention in order to improve the applicability of the polymerizable composition. In this case, it is preferable to remove the organic solvent by natural drying, drying by heating, drying under reduced pressure, drying by heating under reduced pressure, or the like, after applying the polymerizable composition to the substrate.

The polymerizable compound according to one embodiment of the invention or the polymerizable composition according to one embodiment of the invention may be polymerized by applying activated energy rays, or utilizing a thermal polymerization method, for example. It is preferable to polymerize the polymerizable compound or the polymerizable composition by applying activated energy rays since heating is unnecessary (i.e., the reaction can be effected at room temperature). It is preferable to apply light (e.g., ultraviolet rays) to the polymerizable compound or the polymerizable composition since the operation is simple.

The temperature during application is preferably set to 30° C. or less. The irradiance is normally 1 W/m$^2$ to 10 kW/m$^2$, and preferably 5 W/m$^2$ to 2 kW/m$^2$.

A polymer obtained by polymerizing the polymerizable compound according to one embodiment of the invention or the polymerizable composition according to one embodiment of the invention may be removed from the substrate, and used alone, or may be used directly as an optical film organic material or the like without removing the polymer from the substrate.

The number average molecular weight of the polymer according to one embodiment of the invention thus obtained is preferably 500 to 500,000, and more preferably 5,000 to 300,000. When the number average molecular weight of the polymer is within the above range, the resulting film exhibits high hardness and an excellent handling capability. The number average molecular weight of the polymer may be determined by gel permeation chromatography (GPC) using monodisperse polystyrene as a standard (eluent: tetrahydrofuran).

It is considered that the polymer according to one embodiment of the invention has a structure in which crosslinking points are uniformly present within the molecule, and exhibits a high crosslinking efficiency and excellent hardness.

The polymer according to one embodiment of the invention makes it possible to inexpensively produce an optical film that achieves uniform conversion of polarized light over a wide wavelength band, and exhibits satisfactory performance.

4) Optically Anisotropic Article

An optically anisotropic article according to one embodiment of the invention includes (is produced using) the polymer according to one embodiment of the invention.

The optically anisotropic article according to one embodiment of the invention may be obtained by forming an alignment film on a substrate, and forming a polymer film on the alignment film using the polymer according to one embodiment of the invention.

The alignment film is formed on the surface of the substrate in order to achieve the in-plane alignment of an organic semiconductor compound in one direction.

The alignment film may be obtained by applying a solution (alignment film composition) that includes a polymer (e.g., polyimide, polyvinyl alcohol, polyester, polyallylate, polyamideimide, or polyetherimide) to the substrate to form a film, drying the film, and subjecting the film to a rubbing treatment in one direction, for example.

The thickness of the alignment film is preferably 0.001 to 5 μm, and more preferably 0.001 to 1 μm.

The rubbing treatment may be performed on the alignment film, or may be performed on the substrate. The rubbing treatment may be implemented using an arbitrary method. For example, the alignment film may be rubbed in a given direction using a roll around which a cloth or felt formed of synthetic fibers (e.g., nylon) or natural fibers (e.g., cotton) is wound. It is preferable to wash (clean) the alignment film with isopropyl alcohol or the like after completion of the rubbing treatment in order to remove a fine powder (foreign substance) formed during the rubbing treatment, and clean the surface of the alignment film.

The alignment film may be provided with a function of achieving in-plane alignment in one direction by applying polarized UV rays to the surface of the alignment film.

A liquid crystal layer may be formed on the alignment film using the polymer according to one embodiment of the invention by utilizing the method described above in connection with the polymer according to one embodiment of the invention.

Since the optically anisotropic article according to one embodiment of the invention is produced using the polymer according to one embodiment of the invention, the optically anisotropic article can be produced inexpensively, achieves uniform conversion of polarized light over a wide wavelength band, and exhibits satisfactory performance.

The optically anisotropic article according to one embodiment of the invention may be applied as a retardation film, an alignment film for a liquid crystal display device (liquid crystal display), a polarizer, a viewing angle-improving film, a color filter, a low-pass filter, an optical polarization prism, an optical filter, and the like.

EXAMPLES

The invention is further described below by way of examples. Note that the invention is not limited to the following examples.

Example 1

Synthesis of Compound 1

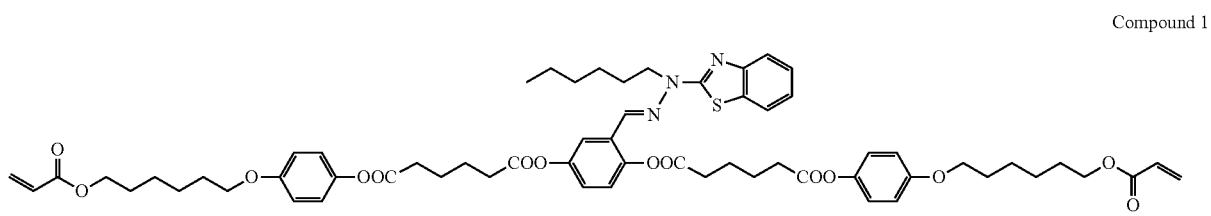

Compound 1

Step 1: Synthesis of Intermediate A

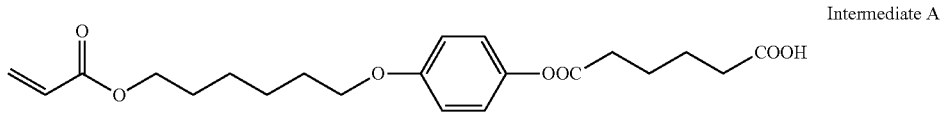

Intermediate A

A three-necked reactor equipped with a thermometer was charged with 18.0 g (123 mmol) of adipic acid and 250 ml of tetrahydrofuran (THF) under a nitrogen stream to prepare a homogeneous solution. The reactor was immersed in an ice bath to adjust the temperature inside the reactor to 0° C. 10.0 g (77.4 mmol) of N,N-diisopropylethylamine was slowly added dropwise to the solution, and a solution prepared by dissolving 4.23 g (36.9 mmol) of methanesulfonyl chloride in 50 ml of THF was slowly added dropwise to the mixture. After the dropwise addition, the mixture was stirred for 45 minutes. 9.5 g (35.9 mmol) of 4-(6-acryloyloxyhex-1-yloxy)phenol (manufactured by DKSH Japan K.K.) was added to the resulting reaction mixture to prepare a solution. 6.0 g (46.4 mmol) of N,N-diisopropylethylamine was slowly added dropwise to the solution. After the dropwise addition, 0.38 g (3.1 mmol) of 4-(dimethylamino)pyridine was added to the mixture. The reaction mixture was returned to room temperature (23° C.), and stirred for 4 hours.

After completion of the reaction, the reaction mixture was added to 1 l of dilute hydrochloric acid, followed by extraction twice with 300 ml of ethyl acetate. The organic layer was collected and dried over anhydrous sodium sulfate, and sodium sulfate was filtered off. The solvent was removed from the filtrate using a rotary evaporator to obtain a light yellow oil. The light yellow oil was purified by silica gel column chromatography (toluene:ethyl acetate=5:5 (volume ratio)), and purified by silica gel column chromatography (chloroform:methanol=95:5 (volume ratio)) to obtain 4.0 g of an intermediate A as a white solid (yield: 28.4%).

The structure of the target product was identified by $^1$H-NMR.

$^1$H-NMR (500 MHz, CDCl$_3$, TMS, δ ppm): 12.2-10.0 (br, 1H), 6.97 (d, 2H, J=9.0 Hz), 6.86 (d, 2H, J=9.0 Hz), 6.40 (dd, 1H, J=1.5 Hz, 17.5 Hz), 6.12 (dd, 1H, J=10.5 Hz, 17.5 Hz), 5.82 (dd, 1H, J=1.5 Hz, 10.5 Hz), 4.17 (t, 2H, J=6.5 Hz), 3.93 (t, 2H, J=6.5 Hz), 2.57 (t, 2H, J=7.0 Hz), 2.43 (t, 2H, J=7.0 Hz), 1.85-1.67 (m, 8H), 1.55-1.40 (m, 4H)

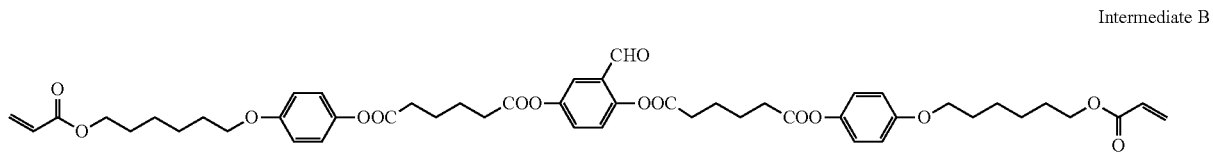

Intermediate B

Step 2: Synthesis of Intermediate B

A three-necked reactor equipped with a thermometer was charged with 4.0 g (10.2 mmol) of the intermediate A, 100 ml of THF, and 1 ml of N,N-dimethylformamide (DMF) under a nitrogen stream to prepare a homogeneous solution. The reactor was immersed in an ice water bath to adjust the temperature inside the reactor to 10° C. A solution prepared by dissolving 13.6 g (0.11 mol) of oxalyl chloride in 50 ml of THF was slowly added to the solution contained in the reactor while maintaining the temperature of the reaction mixture at 10 to 20° C. The reaction mixture was then returned to room temperature (23° C.), and stirred at 23° C. for 6 hours. After completion of the reaction, the reaction mixture was concentrated using a rotary evaporator to obtain a yellow oil. The yellow oil was used directly for the subsequent reaction without purification.

Another three-necked reactor equipped with a thermometer was charged with 0.5 g (3.6 mmol) of 2,5-dihydroxybenzaldehyde, 1.2 g (9.3 mmol) of N,N-diisopropylethylamine, 0.2 g (1.6 mmol) of 4-(dimethylamino)pyridine, and 100 ml of THF under a nitrogen stream to prepare a homogeneous solution. A solution prepared by dissolving the yellow oil in 80 ml of THF was slowly added dropwise to the solution in an ice bath. After the dropwise addition, the reaction mixture was returned to room temperature (23° C.), and stirred for 6 hours. After completion of the reaction, the reaction mixture was added to 500 ml of dilute hydrochloric acid, and extracted twice with 150 ml of ethyl acetate. The organic layer was collected and dried over anhydrous sodium sulfate, and sodium sulfate was filtered off. The solvent was removed from the filtrate using a rotary evaporator to obtain a yellow oil. The yellow solid was purified by silica gel column chromatography (toluene:ethyl acetate=8:2 (volume ratio)) to obtain 1.8 g of an intermediate B as a white solid (yield: 56.4%).

The structure of the target product was identified by $^1$H-NMR.

$^1$H-NMR (500 MHz, CDCl$_3$, TMS, δ ppm): 10.06 (s, 1H), 7.63 (d, 1H, J=2.5 Hz), 7.37 (dd, 1H, J=2.5 Hz, 9.0 Hz), 7.21 (d, 1H, J=9.0 Hz), 6.99 (d, 4H, J=9.0 Hz), 6.87 (d, 4H, J=9.0 Hz), 6.40 (dd, 2H, J=1.5 Hz, 17.5 Hz), 6.12 (dd, 2H, J=10.5 Hz, 17.5 Hz), 5.82 (dd, 2H, J=1.5 Hz, 10.5 Hz), 4.17 (t, 4H, J=6.5 Hz), 3.93 (t, 4H, J=6.5 Hz), 2.75-2.59 (m, 8H), 1.95-1.64 (m, 16H), 1.55-1.40 (m, 8H)

Step 3: Synthesis of Intermediate C

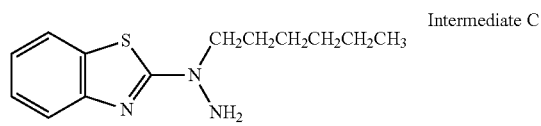

Intermediate C

A four-necked reactor equipped with a thermometer was charged with 2.00 g (12.1 mmol) of 2-hydrazinobenzothiazole and 20 ml of DMF under a nitrogen stream to prepare a solution. After the addition of 8.36 g (60.5 mmol) of potassium carbonate and 3.08 g (14.5 mmol) of 1-iodohexane to the solution, the mixture was stirred at 50° C. for 7 hours. The resulting reaction mixture was cooled to 20° C., added to 200 ml of water, and extracted with 300 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a yellow solid. The yellow solid was purified by silica gel column chromatography (n-hexane:ethyl acetate=75:25 (volume ratio)) to obtain 2.10 g of an intermediate C as a white solid (yield: 69.6%).

The structure of the target product was identified by $^1$H-NMR.

$^1$H-NMR (500 MHz, CDCl$_3$, TMS, δ ppm): 7.60 (dd, 1H, J=1.0 Hz, 8.0 Hz), 7.53 (dd, 1H, J=1.0 Hz, 8.0 Hz), 7.27 (ddd, 1H, J=1.0 Hz, 8.0 Hz, 8.0 Hz), 7.06 (ddd, 1H, J=1.0 Hz, 8.0 Hz, 8.0 Hz), 4.22 (s, 2H), 3.74 (t, 2H, J=7.5 Hz), 1.69-1.76 (m, 2H), 1.29-1.42 (m, 6H), 0.89 (t, 3H, J=7.0 Hz)

Step 4: Synthesis of Compound 1

A four-necked reactor equipped with a thermometer was charged with 1.5 g (1.69 mmol) of the intermediate B synthesized in the step 2, 0.464 g (1.86 mmol) of the intermediate C synthesized in the step 3, and 50 ml of THF under a nitrogen stream to prepare a solution. After the addition of 39.3 mg (0.17 mmol) of (±)-10-camphorsulfonic acid to the solution, the mixture was stirred at room temperature (23° C.) for 7 hours. After completion of the reaction, the reaction mixture was added to 300 ml of diluted sodium bicarbonate water, and extracted twice with 150 ml of ethyl acetate. The ethyl acetate layer was collected and dried over anhydrous sodium sulfate, and sodium sulfate was filtered off. Ethyl acetate was evaporated from the filtrate under reduced pressure using a rotary evaporator to obtain a light yellow oil. The light yellow oil was purified by silica gel column chromatography (toluene:ethyl acetate=80:20 (volume ratio)) to obtain 1.2 g of a compound 1 as a light yellow oil (yield: 63.5%).

The structure of the target product was identified by $^1$H-NMR.

$^1$H-NMR (500 MHz, CDCl$_3$, TMS, δ ppm): 7.74 (d, 1H, J=3.0 Hz), 7.67-7.60 (m, 3H), 7.35-7.31 (m, 1H), 7.15-7.09 (m, 3H), 7.00-6.96 (m, 4H), 6.85 (d, 4H, J=9.0 Hz), 6.40 (dd, 2H, J=1.5 Hz, 17.5 Hz), 6.12 (dd, 2H, J=10.5 Hz, 17.5 Hz), 5.81 (dd, 2H, J=1.5 Hz, 10.5 Hz), 4.28 (t, 2H, J=7.5 Hz), 4.17 (t, 2H, J=6.5 Hz), 4.16 (t, 2H, J=6.5 Hz), 3.911 (t, 2H, J=6.5 Hz), 3.909 (t, 2H, J=6.5 Hz), 2.72-2.61 (m, 8H), 1.93-1.67 (m, 16H), 1.52-1.27 (m, 16H), 0.89 (t, 3H, J=7.0 Hz)

Synthesis Example 1

Synthesis of Compound α

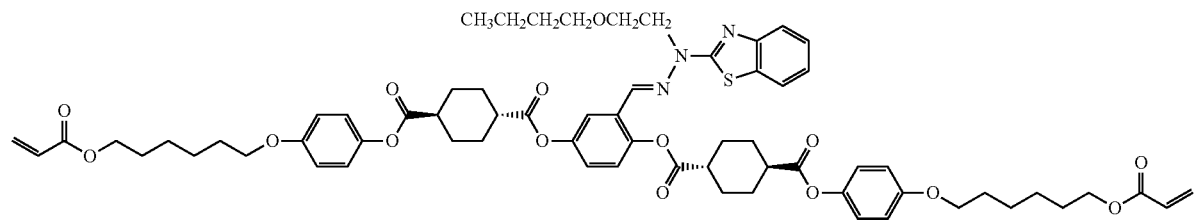

Compound α

Step 1: Synthesis of Intermediate X

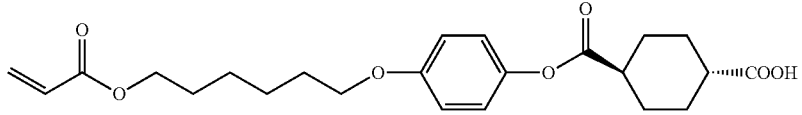

Intermediate X

A three-necked reactor equipped with a thermometer was charged with 17.98 g (104.42 mmol) of trans-1,4-cyclohexanedicarboxylic acid and 180 ml of THF under a nitrogen stream. After the addition of 6.58 g (57.43 mmol) of methanesulfonyl chloride to the mixture, the reactor was immersed in a water bath to adjust the temperature inside the reactor to 20° C. 6.34 g (62.65 mmol) of triethylamine was added dropwise to the reaction mixture over 10 minutes while maintaining the temperature inside the reactor at 20 to 30° C. After the dropwise addition, the water bath was removed, and the mixture was stirred at room temperature (23° C.) for 2 hours. After the addition of 0.64 g (5.22 mmol) of 4-(dimethylamino)pyridine and 13.80 g (52.21 mmol) of 4-(6-acryloyloxyhex-1-yloxy)phenol to the reaction mixture, the reactor was immersed in a water bath to adjust the temperature inside the reactor to 15° C. 6.34 g (62.65 mmol) of triethylamine was added dropwise to the reaction mixture over 10 minutes while maintaining the temperature inside the reactor at 20 to 30° C. After the dropwise addition, the mixture was stirred at room temperature (23° C.) for 2 hours. After completion of the reaction, 1,000 ml of distilled water and 100 ml of a saturated sodium chloride solution were added to the reaction mixture, followed by extraction twice with 400 ml of ethyl acetate. The organic layer was collected and dried over anhydrous sodium sulfate, and sodium sulfate was filtered off. The filtrate was concentrated using a rotary evaporator, and the concentrate was purified by silica gel column chromatography (THF:toluene=1:9 (volume ratio)) to obtain 14.11 g of an intermediate X (yield: 65%).

The structure of the target product was identified by $^1$H-NMR.

$^1$H-NMR (500 MHz, DMSO-$d_6$, TMS, δ ppm): 12.12 (s, 1H), 6.99 (d, 2H, J=9.0 Hz), 6.92 (d, 2H, J=9.0 Hz), 6.32 (dd, 1H, J=1.5 Hz, 17.5 Hz), 6.17 (dd, 1H, J=10.0 Hz, 17.5 Hz), 5.93 (dd, 1H, J=1.5 Hz, 10.0 Hz), 4.11 (t, 2H, J=6.5 Hz), 3.94 (t, 2H, J=6.5 Hz), 2.48-2.56 (m, 1H), 2.18-2.26 (m, 1H), 2.04-2.10 (m, 2H), 1.93-2.00 (m, 2H), 1.59-1.75 (m, 4H), 1.35-1.52 (m, 8H)

Step 2: Synthesis of Intermediate Y

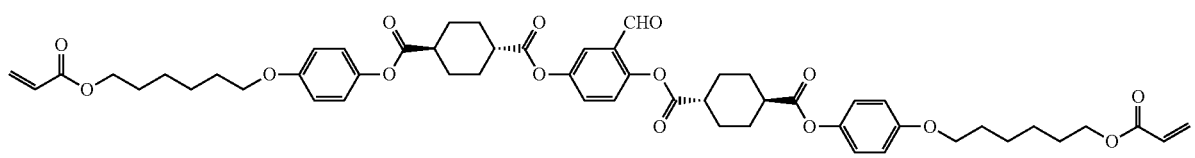

Intermediate Y

A three-necked reactor equipped with a thermometer was charged with 4.00 g (9.56 mmol) of the intermediate X and 60 ml of THF under a nitrogen stream to prepare a solution. After the addition of 1.12 g (9.78 mmol) of methanesulfonyl chloride to the solution, the reactor was immersed in a water bath to adjust the temperature inside the reactor to 20° C. 1.01 g (9.99 mmol) of triethylamine was added dropwise to the reaction mixture over 5 minutes while maintaining the temperature inside the reactor at 20 to 30° C. After removing the water bath, the mixture was stirred at room temperature (23° C.) for 2 hours. After the addition of 0.11 g (0.87 mmol) of 4-(dimethylamino)pyridine and 0.60 g (4.35 mmol) of 2,5-dihydroxybenzaldehyde to the reaction mixture, the reactor was immersed in a water bath to adjust the temperature inside the reactor to 15° C. 1.10 g (10.87 mmol) of triethylamine was added dropwise to the reaction mixture over 5 minutes while maintaining the temperature inside the reactor at 20 to 30° C. After the dropwise addition, the mixture was stirred at room temperature (23° C.) for 2 hours. After completion of the reaction, 400 ml of distilled water and 50 ml of a saturated sodium chloride solution were added to the reaction mixture, followed by extraction twice with 750 ml of ethyl acetate. The organic layer was collected and dried over anhydrous sodium sulfate, and sodium sulfate was filtered off. The filtrate was concentrated using a rotary evaporator to obtain a solid. The solid was dissolved in 100 ml of THF. 500 ml of methanol was added to the solution to precipitate crystals, which were filtered off. The crystals were washed with methanol, and dried under vacuum to obtain 2.51 g of an intermediate Y (yield: 62%).

The structure of the target product was identified by $^1$H-NMR.

$^1$H-NMR (500 MHz, DMSO-$d_6$, TMS, δ ppm): 10.02 (s, 1H), 7.67 (d, 1H, J=3.0 Hz), 7.55 (dd, 1H, J=3.0 Hz, 8.5 Hz), 7.38 (d, 1H, J=8.5 Hz), 6.99-7.04 (m, 4H), 6.91-6.96 (m, 4H), 6.32 (dd, 2H, J=1.5 Hz, 17.5 Hz), 6.17 (dd, 2H, J=10.0 Hz, 17.5 Hz), 5.93 (dd, 2H, J=1.5 Hz, 10.0 Hz), 4.11 (t, 4H, J=6.5 Hz), 3.95 (t, 4H, J=6.5 Hz), 2.56-2.81 (m, 4H), 2.10-2.26 (m, 8H), 1.50-1.76 (m, 16H), 1.33-1.49 (m, 8H)

Step 3: Synthesis of Intermediate Z

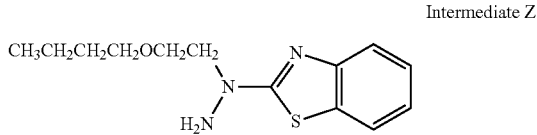

Intermediate Z

A three-necked reactor equipped with a thermometer was charged with 2.00 g (12.1 mmol) of 2-hydrazinobenzothiazole and 30 ml of DMF under a nitrogen stream to prepare a solution, and 7.88 g (24.2 mmol) of cesium carbonate was added to the solution. 1.98 g (14.5 mmol) of butyl 2-chloroethyl ether was added dropwise to the mixture at 0° C. over 5 minutes. After the dropwise addition, the reaction mixture was returned to room temperature (23° C.), and stirred for 3 hours. After completion of the reaction, 200 ml of water was added to the reaction mixture, followed by extraction twice with 100 ml of ethyl acetate. The organic layer was collected and dried over anhydrous sodium sulfate, and sodium sulfate was filtered off The filtrate was concentrated using a rotary evaporator, and the concentrate was purified by silica gel column chromatography (n-hexane:ethyl acetate=75:25 (volume ratio)) to obtain 1.70 g of an intermediate Z as a white solid (yield: 53.0%).

The structure of the target product was identified by $^1$H-NMR.

$^1$H-NMR (500 MHz, CDCl$_3$, TMS, δ ppm): 7.61 (dd, 1H, J=1.0 Hz, 8.0 Hz), 7.50 (dd, 1H, J=1.0 Hz, 8.0 Hz), 7.27-7.29 (m, 1H), 7.04-7.08 (m, 1H), 4.70 (s, 2H), 4.01 (t, 2H, J=5.0 Hz), 3.82 (t, 2H, J=5.0 Hz), 3.44 (t, 2H, J=7.0 Hz), 1.52-1.57 (m, 2H), 1.31-1.39 (m, 2H), 0.90 (t, 3H, J=7.0 Hz)

Step 4: Synthesis of Compound α

A three-necked reactor equipped with a thermometer was charged with 1.50 g (1.60 mmol) of the intermediate Y synthesized in the step 2, 369 mg (1.78 mmol) of the intermediate Z synthesized in the step 3, 41.4 mg (0.178 mmol) of (±)-10-camphorsulfonic acid, 16 ml of THF, and 4 ml of ethanol under a nitrogen stream to prepare a homogeneous solution. The solution was stirred at 40° C. for 5 hours. After completion of the reaction, the reaction mixture was added to 100 ml of water, and extracted with 200 ml of ethyl acetate. After drying the ethyl acetate layer over anhydrous sodium sulfate, sodium sulfate was filtered off. Ethyl acetate was evaporated from the filtrate under reduced pressure using a rotary evaporator to obtain a yellow solid. The yellow solid was purified by silica gel column chromatography (toluene:ethyl acetate=9:1 (volume ratio)) to obtain 1.31 g of a compound α as a light yellow solid (yield: 69.4%).

The structure of the target product was identified by $^1$H-NMR.

$^1$H-NMR (500 MHz, CDCl$_3$, TMS, δ ppm): 8.03 (s, 1H), 7.76 (d, 1H, J=1.5 Hz), 7.65-7.71 (m, 2H), 7.34 (ddd, 1H, J=1.5 Hz, 8.0 Hz, 8.0 Hz), 7.17 (ddd, 1H, J=1.5 Hz, 8.0 Hz, 8.0 Hz), 7.09-7.12 (m, 2H), 6.96-7.00 (m, 4H), 6.87-6.90 (m, 4H), 6.40 (dd, 2H, J=1.5 Hz, 17.5 Hz), 6.13 (dd, 2H, J=10.5 Hz, 17.5 Hz), 5.82 (dd, 2H, J=1.5 Hz, 10.5 Hz), 4.45 (t, 2H, J=5.5 Hz), 4.18 (t, 4H, J=7.0 Hz), 3.95 (t, 4H, J=7.0 Hz), 3.79 (t, 2H, J=5.5 Hz), 3.44 (t, 2H, J=7.0 Hz), 2.55-2.74 (m, 4H), 2.28-2.40 (m, 8H), 1.65-1.83 (m, 16H), 1.42-1.55 (m, 10H), 1.25-1.34 (m, 2H), 0.85 (t, 3H, J=7.0 Hz)

The phase transition temperature was measured by the following method using the compound 1 obtained in Example 1, the compound α obtained in Synthesis Example 1, and the compound 1r ("LC242" manufactured by BASF) of Reference Example 1 that was used in Comparative Examples 1 and 2.

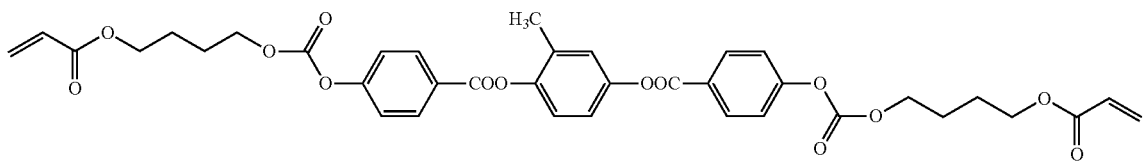

Compound 1r

Measurement of Phase Transition Temperature 10 mg of each compound (compounds 1, α, and 1r) was weighed, and placed in a solid state between two glass substrates provided with a polyimide alignment film subjected to a rubbing treatment (manufactured by E.H.C. Co., Ltd.). The substrates were placed on a microscope cooling-heating device ("10036" manufactured by Japan High Tech Co., Ltd.), heated from −10° C. to +200° C., and cooled to 23° C. A change in structure during a change in temperature was observed using a polarizing optical microscope ("ECLIPSE LV100POL" manufactured by Nikon Corporation).

The phase transition temperature measurement results are shown in Table 1.

In Table 1, "C" refers to "crystal", "N" refers to "nematic", and "I" refers to "isotropic". The term "crystal" means that the test compound was in a solid phase, the term "nematic" means that the test compound was in a nematic liquid crystal phase, and the term "isotropic" means that the test compound was in an isotropic liquid phase.

TABLE 1

| | Compound | Phase transition temperature |
|---|---|---|
| Example 1 | Compound 1 | C ⇌ I (15° C. / 23° C. or less) |
| Synthesis Example 1 | Compound α | C ⇌ N ⇌ I (110° C. / 23° C. or less, 216° C. / 210° C.) |
| Reference Example 1 | Compound 1r | C ⇌ N ⇌ I (60° C. / 23° C. or less, 123° C. / 122° C.) |

Example 2

0.3 g of the compound 1 obtained in Example 1, 0.7 g of the compound α obtained in Synthesis Example 1, 30 mg of a photoinitiator ("Adekaoptomer N-1919" manufactured by Adeka Corporation), and 100 mg of a 1% cyclopentanone solution of a surfactant ("KH-40" manufactured by AGC Seimi Chemical Co., Ltd.) were dissolved in 2.3 g of cyclopentanone. The solution was filtered through a disposable filter having a pore size of 0.45 μm to prepare a polymerizable composition 1.

Reference Examples 1 and 2

A polymerizable composition 2 was prepared in the same manner as in Example 2, except that 1.0 g of the compound α obtained in Synthesis Example 1 was used instead of using 03 g of the compound 1 and 0.7 g of the compound α.

Comparative Example 1

A polymerizable composition 3 was prepared in the same manner as in Example 2, except that 0.3 g of the compound 1r was used instead of 0.3 g of the compound 1.

Comparative Example 2

A polymerizable composition 4 was prepared in the same manner as in Example 2, except that 1.0 g of the compound 1r was used instead of using 0.3 g of the compound 1 and 0.7 g of the compound α.

Each of the polymerizable compositions 1 to 4 was polymerized using the following method to obtain a polymer. The retardation and the wavelength dispersion were measured and evaluated using the resulting polymer.
Measurement of Retardation and Evaluation of Wavelength Dispersion polyimide alignment film subjected to a rubbing treatment (manufactured by E.H.C. Co., Ltd.) using a #4 wire bar. The resulting film was dried for 1 minute at the temperature shown in Table 2, and subjected to an alignment treatment for 1 minute at the temperature shown in Table 2 to form a liquid crystal layer. UV rays were applied (directly) to the liquid crystal layer at a dose of 2,000 mJ/cm$^2$ to effect polymerization to prepare a wavelength dispersion measurement sample.

(ii) Measurement of Retardation

The retardation of the sample between 400 nm and 800 nm was measured using an ellipsometer ("M2000U" manufactured by J. A. Woollam).

(iii) Evaluation of Wavelength Dispersion

The wavelength dispersion was evaluated based on the values α and β that were calculated by the following expressions using the measured retardation.

α=(retardation at 449.9 nm)/(retardation at 548.5 nm)
β=(retardation at 650.2 nm)/(retardation at 548.5 nm)

The value α is smaller than 1, and the value β is larger than 1 when ideal wideband wavelength dispersion (reverse wavelength dispersion) is achieved. The value α and the value β are almost identical to each other when flat wavelength dispersion is achieved. The value α is larger than 1, and the value β is smaller than 1 when normal dispersion is achieved.

Flat wavelength dispersion in which the value α and the value β are almost identical to each other is preferable, and reverse wavelength dispersion in which the value α is smaller than 1, and the value β is larger than 1, is particularly preferable.

Table 2 shows the thickness (μm) of the polymer film, the retardation (Re) at a wavelength of 548.5 nm, and the values α and β. Note that "NA" in Table 2 means that the corresponding value was not measured.

TABLE 2

| | Polymerizable composition | Polymerizable compound 1 Compound | Ratio (%) | Polymerizable compound 2 Compound | Ratio (%) | Drying temperature (° C.) | Alignment treatment temperature (° C.) |
|---|---|---|---|---|---|---|---|
| Example 2 | 1 | Compound α | 70 | Compound 1 | 30 | 110 | 23 |
| Reference Example 1 | 2 | Compound α | 100 | — | — | 120 | 23 |
| Reference Example 2 | 2 | Compound α | 100 | — | — | 110 | 23 |
| Comparative Example 1 | 3 | Compound α | 70 | Compound 1r | 30 | 70 | 23 |
| Comparative Example 2 | 4 | Compound 1r | 100 | — | — | 80 | 23 |

| | State of film | Thickness (μm) | Re (548.5 nm) | α | β |
|---|---|---|---|---|---|
| Example 2 | Transparent | 1.435 | 105.43 | 0.839 | 1.030 |
| Reference Example 1 | Transparent | 1.669 | 123.98 | 0.841 | 1.027 |
| Reference Example 2 | Cloudy | NA | NA | NA | NA |
| Comparative Example 1 | Transparent | 1.533 | 155.66 | 1.022 | 0.985 |
| Comparative Example 2 | Transparent | 1.479 | 222.9 | 1.086 | 0.970 |

(i) Formation of Liquid Crystal Layer Using Polymerizable Composition

Each of the polymerizable compositions 1 to 4 was applied to a transparent glass substrate provided with a The following were confirmed from the results shown in Table 2.

The polymer obtained by polymerizing the compound α had reverse wavelength dispersion in which the value α was smaller than 1, and the value β was larger than 1 (see the results for the value α and the value β of Reference Example 1). The value α and the value β of the polymer (Example 2) obtained by polymerizing the mixture including the compound α and the compound 1 were almost identical to those of the polymer (Reference Example 1) obtained by polymerizing the compound α.

It was confirmed from the results of Reference Example 2 that the drying temperature can be reduced by producing a polymer by polymerizing a mixture including the compound α and the compound 1 (Example 2) as compared with the case of polymerizing only the compound α.

On the other hand, the polymer obtained by polymerizing the compound 1r had normal dispersion (see the results for the value α and the value β of Comparative Example 2). The polymer (Comparative Example 1) obtained by polymerizing the mixture including the compound α and the compound 1r had normal dispersion in which the value α was larger than 1, and the value β was smaller than 1. It was thus confirmed that a polymer obtained by polymerizing the compound 1 of Example 1 has the same wavelength dispersion as that of the polymer obtained by polymerizing the compound α.

Specifically, a polymer obtained by polymerizing the compound 1 has reverse wavelength dispersion, and the compound 1 is useful as a raw material for producing a polymer having wavelength dispersion. Since the drying temperature employed when forming a liquid crystal layer can be reduced while maintaining the reverse wavelength dispersion, it is possible to improve the energy efficiency, and reduce the cost required to produce a liquid crystal polymer film.

The invention claimed is:

1. A polymerizable compound represented by a formula (I),

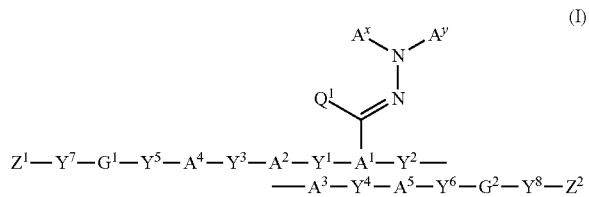

wherein each of $Y^1$ to $Y^8$ independently represents a chemical single bond, —O—, —S—, —O—C(=O)—, —C(=O)—O—, —O—C(=O)—O—, —NR$^1$—C(=O)—, —C(=O)—NR$^1$—, —O—C(=O)—NR$^1$—, —NR$^1$—C(=O)—O—, —NR$^1$—C(=O)—NR$^1$—, —O—NR$^1$—, or —NR$^1$—O—, $R^1$ is a hydrogen atom or an alkyl group having 1 to 6 carbon atoms, each of $A^2$, $A^3$, $G^1$, and $G^2$ independently represents a substituted or unsubstituted divalent linear aliphatic group having 1 to 20 carbon atoms that optionally includes —O—, —S—, —O—C(=O)—, —C(=O)—O—, —O—C(=O)—O—, —NR$^2$—C(=O)—, —C(=O)—NR$^2$—, —NR$^2$—, or —C(=O)—, provided that a case where the linear aliphatic group includes two or more adjacent —O— or —S— is excluded, $R^2$ represents a hydrogen atom or an alkyl group having 1 to 6 carbon atoms, each of $Z^1$ and $Z^2$ independently represents an alkenyl group having 2 to 10 carbon atoms that is substituted with a halogen atom, or unsubstituted, $A^x$ represents an organic group having 2 to 30 carbon atoms that includes at least one aromatic ring selected from a group consisting of an aromatic hydrocarbon ring and a hetcroaromatic ring, $A^y$ represents a hydrogen atom, a substituted or unsubstituted alkyl group having 1 to 20 carbon atoms, a substituted or unsubstituted alkenyl group having 2 to 20 carbon atoms, a substituted or unsubstituted cycloalkyl group having 3 to 12 carbon atoms, a substituted or unsubstituted alkynyl group having 2 to 20 carbon atoms, —C(=O)—R$^3$, —SO$_2$—R$^4$, —C(=S)NH—R$^5$, or an organic group having 2 to 30 carbon atoms that includes at least one aromatic ring selected from the group consisting of an aromatic hydrocarbon ring and a heteroaromatic ring, $R^3$ represents a substituted or unsubstituted alkyl group having 1 to 20 carbon atoms, a substituted or unsubstituted alkenyl group having 2 to 20 carbon atoms, or a substituted or unsubstituted cycloalkyl group having 3 to 12 carbon atoms, $R^4$ represents an alkyl group having 1 to 20 carbon atoms, an alkenyl group having 2 to 20 carbon atoms, a phenyl group, or a 4-methylphenyl group, $R^5$ represents a substituted or unsubstituted alkyl group having 1 to 20 carbon atoms, a substituted or unsubstituted alkenyl group having 2 to 20 carbon atoms, a substituted or unsubstituted cycloalkyl group having 3 to 12 carbon atoms, or a substituted or unsubstituted aromatic group having 5 to 20 carbon atoms, provided that the aromatic ring included in $A^x$ and the aromatic ring optionally included in $A^y$ are either substituted or unsubstituted, and $A^1$ and $A^y$ are optionally bonded to each other to form a ring, $A^1$ represents a substituted or unsubstituted trivalent aromatic group, each of $A^4$ and $A^5$ independently represents a substituted or unsubstituted divalent aromatic group having 6 to 30 carbon atoms, and $Q^1$ represents a hydrogen atom, or a substituted or unsubstituted alkyl group having 1 to 6 carbon atoms.

2. The polymerizable compound according to claim 1, wherein at least one of $A^x$ and $A^y$ include π electrons and a total number of the π electrons included in $A^x$ and $A^y$ is 4 to 24.

3. The polymerizable compound according to claim 1, wherein $A^1$ is a substituted or unsubstituted trivalent benzene ring group, or a substituted or unsubstituted trivalent naphthalene ring group.

4. The polymerizable compound according to claim 1, wherein each of $Y^1$ to $Y^8$ independently represents a chemical single bond, —O—, —O—C(=O)—, —C(=O)—O—, or —O—C(=O)—O—.

5. The polymerizable compound according to claim 1, wherein each of $Z^1$ and $Z^2$ independently represents $CH_2$=CH—, $CH_2$=C($CH_3$)—, or $CH_2$=C(Cl)—.

6. The polymerizable compound according to claim 1, wherein each of $A^2$, $A^3$, $G^1$, and $G^2$ independently represents a substituted or unsubstituted divalent linear aliphatic group having 1 to 20 carbon atoms that optionally includes —O—, —O—C(=O)—, —C(=O)—O—, or —C(=O)—, provided that a case where the linear aliphatic group includes two or more contiguous —O— is excluded.

7. The polymerizable compound according to claim 1, wherein each of $G^1$ and $G^2$ independently represents an alkylene group having 1 to 12 carbon atoms.

8. A polymerizable composition comprising at least one polymerizable compound according to claim 1.

9. A polymerizable composition comprising at least one polymerizable compound according to claim 1, and an initiator.

10. A polymer obtained by polymerizing the polymerizable compound according to claim 1.

11. The polymer according to claim 10, the polymer being a liquid crystalline polymer.

12. An optically anisotropic article comprising the polymer according to claim 11.

13. A polymer obtained by polymerizing the polymerizable composition according to claim 8.

* * * * *